US007674597B2

(12) United States Patent
Malinin et al.

(10) Patent No.: US 7,674,597 B2
(45) Date of Patent: Mar. 9, 2010

(54) SIGNALING INTERMEDIATES IN AN IN VITRO MODEL OF ALZHEIMER'S DISEASE

(75) Inventors: Nikolay Malinin, Toronto (CA); Maile Skomp, Keaau, HI (US); Sarah Wright, San Francisco, CA (US); Irene Griswold-Prenner, San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/193,353

(22) Filed: Aug. 1, 2005

(65) Prior Publication Data

US 2006/0159674 A1    Jul. 20, 2006

Related U.S. Application Data

(60) Provisional application No. 60/592,393, filed on Aug. 2, 2004.

(51) Int. Cl.
*G01N 33/567* (2006.01)
*G01N 33/53* (2006.01)

(52) U.S. Cl. ................. 435/7.21; 435/7.9; 435/7.92
(58) Field of Classification Search ........................ None
See application file for complete search history.

(56) References Cited

FOREIGN PATENT DOCUMENTS

| WO | WO 97/40072 | 10/1997 |
| WO | WO 00/56871 | 9/2000 |
| WO | WO 03/068808 | 8/2003 |
| WO | WO 2006/014903 A2 | 2/2006 |

OTHER PUBLICATIONS

Michaelis et al., 1998, J. Neurochem., vol. 70, No. 4, pp. 1623-1627.*
Abram, C.L. et al., "The Adaptor Protein Fish Associates with Members of the ADAMs Family and Localizes to Podosomes of Src-transformed Cells," *The Journal of Biological Chemistry*, 276(19), 16844-16851, 2003.
Bernstein, H. et al., "ADAM (A Disintegrin and Metalloprotease) 12 Is Expressed in Rat and Human Brain and Localized to Oligodendrocytes," *Journal of Neuroscience Research*, 75, 353-360, 2004.
Lock, P. et al., "A New Method for Isolating Tyrosine Kinase Substrates Used to Identify Fish, an SH3 and PX Domain-containing Protein, and Src Substrate," *The Embo Journal*, 17(15), 4346-4357, 1998.
Malinin, N.L. et al., "Amyloid-β Neurotoxicity Is Mediated by FISH Adapter Protein and ADAM12 Metalloprotease Activity," *PNAS*, 102(8),3058-3063, 2005.

* cited by examiner

*Primary Examiner*—Olga N Chernyshev
(74) *Attorney, Agent, or Firm*—Townsend and Townsend and Crew LLP

(57) ABSTRACT

The invention provides a novel human protein, FISH adaptor protein, involved in amyloid β-protein-mediated cell death. Also provided are methods for modulating amyloid β-protein-mediated cell death using agents that interfere with the activity of FISH adaptor protein.

1 Claim, 12 Drawing Sheets

FISH 348-1105

FISH 981-1105

FISH 348-911

SIGNALING INTERMEDIATES IN AN IN VITRO MODEL OF ALZHEIMER'S DISEASE

This application claims the benefit of U.S. Provisional Application No. 60/592,393, filed Aug. 2, 2004, which is incorporated herein by reference in its entirety.

FIELD OF THE INVENTION

This invention relates to identifying proteins involved in mediating neuronal cell death. More specifically, this invention relates to identifying proteins involved in neuronal cell death induced by amyloid-beta protein and the use of such proteins in developing therapies for the treatment of neurodegenerative diseases, such as Alzheimer's disease.

BACKGROUND OF THE INVENTION

Alzheimer's disease (AD) is a progressive neurodegenerative disease resulting in senile dementia and afflicts four million people in the United States alone (see generally Sloe, TINS, 16:403-409 (1993); Hardy et al., WO 92/13069; Sloe, J. Neuropathol. Exp. Neurol., 53:438-447 (1994); Duff et al., Nature, 373:476-477 (1995); Games et al., Nature, 373:523 (1995)). Broadly speaking, the disease falls into two categories: late onset, which occurs in old age (65+ years); and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, senile plaques and neurofibrillary tangles. Neurofibrillary tangles are intracellular deposits of microtubule-associated tau protein consisting of two filaments twisted about each other in pairs. Senile plaques are areas of disorganized neuropil up to 150 microns across (visible by microscopic analysis of sections of brain tissue) and have extracellular amyloid deposits at the center. A principal component of such plaques is β-amyloid peptide (Aβ) (see Forsyth Phys. Ther., 78:1325-1331 (1998)). Additional proteins found in the plaques include laminin as described by Murtomaki et al., J. Neurosci. Res., 32:261-273 (1992), apoE, acetylcholinesterase, and heparin sulfate proteoglycans, as described by Yan et al., Biochim. Biophys. Acta, 1502:145-57 (2000).

Amyloid precursor protein (APP) is a synaptic single-pass transmembrane protein that is best known for its involvement in AD. In AD patients, amyloid plaques containing aggregated Aβ peptide appear in specific brain regions, triggering an inflammatory response, neuronal cell death, and gradual cognitive decline. One mechanism by which Aβ is derived from APP is cleavage of APP at an extracellular position (β site), followed by an unusual cleavage within the APP transmembrane segment (γ site), producing a fragment of 39-43 amino acids of APP.

Several mutations within the APP protein have been correlated with the presence of Alzheimer's disease (Goate et al., Nature, 349:704-06 (1991) (valine$^{717}$ to isoleucine); Harlin et al., Nature, 353:844-46 (1991) (valine$^{717}$ to glycine); Murrell et al., Science, 254:97-99 (1991) (valine$^{717}$ to phenylalanine); Mullan et al., Nature Genet., 1:345-47 (1992) (a double mutation changing lysine$^{595}$methionine$^{596}$ to asparagine$^{595}$leucine$^{596}$)). Such mutations are thought to cause Alzheimer's disease by increased or altered processing of APP to Aβ, particularly processing of APP to increased amounts of the long form of Aβ (i.e., Aβ -42 and Aβ1-43). Mutations in other genes, such as the presenilin genes PS1 and PS2, are thought to indirectly affect processing of APP to generate increased amounts of long form Aβ (Hardy, TINS, 20:154 (1997)). These observations indicate that Aβ, and particularly its long form, is a causative element in Alzheimer's disease (Velez-Pardo et al., Gen. Pharm., 31(5):675-81 (1998)).

The Aβ peptide has also been implicated in neuropathological defects seen in individuals inflicted with Down's syndrome. For example, almost all individuals with Down's syndrome, who have an extra copy of chromosome 21, show neuropathological changes similar to those seen in Alzheimer's disease, if they survive into their 40s. This has been attributed to excess production of β-amyloid protein, which is encoded by the APP gene on chromosome 21.

Several proteins have been investigated for possible interactions with Aβ. These include the receptor for advanced glycation endproducts, RAGE (see Yan et al., Nature, 382: 685-91 (1996)), the scavenger receptor (Khoury et al., Nature, 382:716-719 (1996); and Paresce et al., Neuron 17:553-65 (1996)), the endoplasmic reticulum-associated amyloid-beta biding protein (ERAB) (Yan et al., Nature, 389: 689-695 (1997)), α4 or α7 nicotinic acetylcholine receptor (Wang et al., J. Neurochem., 75:1155-1161 (2000) and Wang et al., J. Biol. Chem., 275:5626-5632 (2000)), and the low affinity p75 NGF receptor (see Yaar et al., J. Clin. Invest., 100:2333-2340 (1997)). Additionally, Aβ has been reported to mediate adhesion of cells in a β1-integrin subunit-dependent manner when coated onto plates. (Ghiso et al., Biochem. J., 288:1053-59 (1992); Matter et al., J. Cell Bio., 141:1019-1030 (1998)). However, the mechanism(s) by which Aβ may mediate neurodegeneration remains unclear. The existence and nature of other cellular proteins that may have roles in the process is also largely unclear.

Various signaling pathways have been implicated in the pathogenesis of AD, including, p38, erk and c-jun N-terminal kinases (JNK) kinase cascades. For example, chronic stimulation of the JNKs has been shown to cause neuronal cell death in several disease paradigms, including in vitro AD models. Additionally, it has been shown that expression of kinase-deficient JNK3 protects against Aβ-induced cell death. However, it is not entirely clear which of these pathways and/or the signaling molecules are the key players in the development of the disease. Accordingly, elucidation of the signaling pathways as well as the intermediates of those pathways will help in understanding the pathology of AD and in developing therapeutic strategies to combat AD.

SUMMARY OF THE INVENTION

This invention provides human proteins that play a role in neuronal cell death. In particular, this invention relates to identification-of proteins that are involved in the Aβ-induced cell death pathway in an in vitro model for AD.

The present invention is based on the discovery and isolation of a human homolog of a previously described FISH adapter protein (FISH), from embryonic human cortical cells (HOC). This invention is further based on an observation that FISH is phosphorylated in response to neurotoxic forms of Aβ and is likely to serve as a signaling molecule in Aβ induced neuronal cell death, as shown in an in vitro model for AD. FISH also interacts with other proteins, such as ADAM12, in mediating Aβ-induced cell death. The term "FISH" as used herein is understood to refer to proteins named "Tks/FISH" and "Tks5."

The invention further provides screening methods for identifying agents that modulate Aβ induced cell death by contacting Aβ treated neuronal cells with a candidate agent, and detecting the survival rate of Aβ-treated cells in the presence of the agent relative to the survival rate in the absence of the agent. The cells can be contacted with the agent either sequentially or simultaneously with Aβ. It is understood that the cells are contacted with a neurotoxic form of Aβ, as described herein, in order to induce cell death.

In certain embodiments, the screening method for identifying agents that modulate Aβ induced cell death employs two populations of cells: a first population that overexpresses FISH protein and a second population that expresses less FISH protein or no FISH protein. Both populations are treated with Aβ and either sequentially or simultaneously with a candidate agent. The rate or amount of cell death is compared between the two populations. An agent that has a greater effect (either positive or negative) on the cells that overexpress FISH is likely to modulate the activity of the one or more components of the FISH-mediated cell death pathway.

In certain embodiments, the screening method for identifying agents that modulate Aβ induced cell death measures the effect of a candidate agent on Aβ-induced phosphorylation of FISH protein.

In various embodiments, the screening method for identifying agents that modulate Aβ induced cell death measures the effect of a candidate agent on Aβ-induced cleavage of ADAM12 protein.

In certain embodiments, the screening method for identifying agents that modulate Aβ induced cell death measures the effect of a candidate agent on Aβ-induced changes in FISH protein localization.

Generally, an agent that modulates Aβ-induced cell death in a method of the invention, can be a compound that inhibits one or more activities of Aβ, including but not limited to, for example, phosphorylation of a FISH adapter protein by Aβ, interaction of FISH with members of the ADAM family of proteins, and cleavage of ADAM12.

In some embodiments, an agent is an antibody that binds a FISH interacting protein involved in the the Aβ induced cell death pathway. Examples of FISH interacting proteins include, but are not limited to, ADAM 12. An antibody can be a monoclonal or a polyclonal antibody.

In certain embodiments, agents can also be nonantibody peptides and polypeptides, nucleic acids, lipids, carbohydrates, and small molecules that can modulate Aβ-induced cell death.

The present invention provides methods for modulating Aβ-induced neuronal cell death by administering an effective amount of a mutant form of a FISH interacting protein, such as, for example, a mutant of ADAM1 2 lacking metalloproteinase activity, to Aβ treated cells. In some embodiments, the mutant ADAM is a deletion mutant. In certain embodiments, the mutant ADAM12.protein is administered directly to the cell. In some embodiments, the mutant ADAM12 protein is encoded by a nucleic acid administered to the cell.

The present invention also provides methods for modulating Aβ-induced neuronal cell death by administering an effective amount of a mutant FISH protein. In certain embodiments, the invention provides a method for preventing Aβ-induced neuronal cell death by administering an effective amount of a dominant negative mutant of FISH protein. In certain embodiments, the mutant FISH protein is administered directly to the cell. In some embodiments, the mutant FISH protein is encoded by a nucleic acid administered to the cell.

According to the invention, an agent identified by the methods of the invention can be administered to a patient, in a therapeutically effective dose, in order to treat or prevent Aβ-induced cell death. Embodiments include treatment of AD.

The invention further provides agents that disrupt the interaction of FISH with other proteins, such as members of the ADAM family, where the interaction plays a role in Aβ-induced cell death.

The invention also provides methods of treating or preventing AD in a patient by administering an agent that modulates Aβ-induced cell death, for example, by blocking phosphorylation of FISH, blocking the interaction of FISH with a FISH interacting-protein, such as, ADAM12, or decreasing ADAM12 cleavage. Such agents include, but are not limited to, antibodies, nonantibody peptides and polypeptides, nucleic acids, lipids, carbohydrates, and small compounds.

In some methods, the dosage of antibody can be about 0.01 to about 10 mg/kg body weight of the patient.

In some methods, an agent can be administered with a carrier as a pharmaceutical composition.

In some methods, an agent can be administered intraperitoneally, orally, intranasally, subcutaneously, intrathecally, intramuscularly, topically or intravenously.

DETAILED DESCRIPTION OF THE INVENTION

Figure 1:
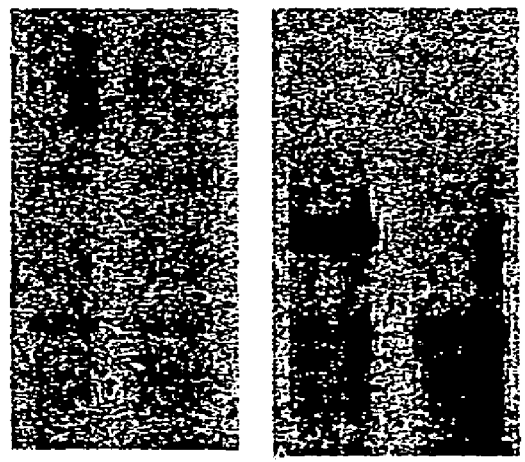
FIG. 1 shows a western blot depicting the cross-reactivity of a protein (p165) in lysates of cultured human cortical cells with an anti-pY845EGFR antibody in the presence or absence of an Aβ peptide (lanes 3 and 4). The western blot also shows the disappearance of cross-reactivity of the p165 protein with the anti-pY845EGFR antibody in lysates of cultured human cortical cells, when the lysates are pretreated with a phosphotyrosine-specific phosphatase (LAR) (lanes 1 and 2).

In order that the present invention be more readily understood, certain terms are first defined. Additional definitions are set forth throughout the detailed description.

The term "antibody" refers to an immunoglobulin, or a fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. It also includes, unless otherwise stated, antibody fragments such as Fab, F(ab')$_2$, Fv, scFv, Fd, dAb, and other antibody fragments which retain the antigen binding function.

The terms "Aβ" and "Aβ peptide" refer to the beta-amyloid protein which is a proteolytic product of the amyloid precursor protein (Aβ P). Aβ is found in senile plaques of brains of individuals affected with Alzheimer's disease (AD) and triggers neuronal cell death, which can be assayed by one or more methods described herein.

The term "ADAM" refers to disintegrin-like and zinc-dependent metalloproteinases that belong to a large protein family. These proteins share all or some of the following domain structure: a signal peptide, a propeptide, a metalloproteinase, a disintegrin, a cysteine-rich and an epidermal growth factor (EGF)-like domain, a transmembrane region, and a cytoplasmic tail. ADAMs are widely distributed in many organs, tissues, and cells, such as brain, testis, epididymis, ovary, breast, placenta, liver, heart, lung, bone, and muscle. These proteins are capable of at least four potential functions: proteolysis, adhesion, fusion, and intracellular signaling, and have been implicated in many diseases. ADAM12, 15, and 19 are members of this family of proteins that have been previously shown to interact with FISH, in particular with the fifth SH3 domain of FISH. (Abram et al., J. Biol. Chem. 278: 16844-16851 (2003)).

The term "Aβ activity" refers to at least one cellular process interrupted or initiated by an Aβ peptide. This term includes signaling pathways involved in Aβ-induced cell death. Generally, Aβ activities include, but are not limited to, tyrosine phosphorylation of FISH, interaction of FISH with FISH interacting proteins, such as ADAM12, and cleavage of ADAM 12, However, an Aβ activity can be any response initiated upon exposure of neuronal cells to a toxic form of Aβ peptide, including, induction of cell death, both in vivo and in vitro.

The terms "FISH" and "FISH adapter protein" refer to a scaffolding protein that contains Five SH3 domains. FISH was first identified as a substrate of the Src protein tyrosine kinase. (Lock et al., The EMBO J., 17: 4346-4357 (1998)). It also contains a Phox homology (PX) domain at the amino-terminus. The fifth SH3 domain has been shown to interact with members of the ADAM family, including, ADAM12, 15, and 19. (Id.)

The nucleic acid sequence of a murine FISH is provided in SEQ ID NO:1 (Genbank Accession Number AJ007012); the amino acid sequence is provided in SEQ ID NO:2.

The term "FISH interacting protein" refers to proteins that cohere with FISH. The term also refers to any variants of such proteins (including splice variants, truncations, fragments, substitutions, addition and deletion mutants, fusion proteins, shuffling sequences and motif sequences, and homologs) that have one or more of the biological activities associated with native proteins, or show disruption of a biological activity associated with the native protein. These proteins further include amino acid sequences that have been modified with conservative or non-conservative changes to the native proteins. These proteins may be derived from any source, natural or synthetic. A FISH interacting protein may either stimulate Aβ-induced cell death or inhibit Aβ-induced cell death. Examples of FISH interacting proteins include members of the ADAM family of proteins, including, ADAM12, 15 and 19, and variants of such proteins, including deletion mutants, such as the ADAM12 deletion mutants described in the Examples herein.

The nucleic acid sequence of a human ADAM12 is provided in SEQ ID NO:3 (GenBank Accession Number BC060804); the amino acid sequence is provided in SEQ ID NO:4.

Additional FISH-interacting proteins can be identified by methods described herein or those well known in the art. For example, co-immunoprecipitation or two-hybrid systems can be used to identify proteins that interact with FISH, which may be involved in the Aβ induced cell death pathway mediated by FISH.

A deletion in a FISH or an ADAM12 protein can be made anywhere in the protein as desirable. A deletion may occur anywhere within the protein; for example, N-terminus, C-terminus or any other part of a FISH protein or an ADAM12 protein. An amino acid deletion according to the invention comprises the removal of at least one amino acid from the N-terminus of a FISH protein. In some embodiments, a deletion comprises removal of at least one amino acid from the C-terminus of a FISH protein. In yet another embodiment, a deletion comprises removal of one or more amino acids from a region lying between the N-terminal end and the C-terminal end of a FISH protein. In one embodiment, such a deletion involves the removal of an entire PX domain of a FISH protein. In certain embodiments, such a deletion involves the removal of an entire SH3 domain of a FISH protein. For example, FISH proteins of the invention comprising a deletion include FISH proteins that have the PX domain deleted or FISH proteins that have one or more of the SH3 domains deleted. Similarly, ADAM proteins can include a deletion of one or more amino acid at the N-terminus, the C-terminus or anywhere in between. Such a deletion may also include the deletion of one or more entire domains, for example, the metalloproteinase domain. Deletions can be generated directly in the FISH or ADAM12 amino acid sequence to make a deletion mutant of the corresponding protein, or they may be generated in a polynucleotide sequence encoding the FISH or ADAM12 protein, thereby making a nucleic acid encoding a deletion mutant of the corresponding protein.

The term "inhibit" or "inhibition" of Aβ activity refers to a reduction, inhibition of otherwise diminution of at least one activity of Aβ due to an agent that effects either phosphorylation of FISH, interaction of FISH with one or more of the FISH interacting proteins, such as ADAM12, or cleavage of ADAM12. Inhibition of a Aβ activity does not necessarily indicate a complete negation of Aβ activity. A reduction in activity can be, for example, at least about 10%, 20%, 30%, 40%, 50%, 60%, 70%, 80%, 90% or more. In certain embodiments, inhibition can be measured by a decrease in FISH phosphorylation. In certain embodiments, the inhibition can be measured by a decrease in ADAM12 cleavage. In some embodiments, the inhibition can be measured by a decrease in heregulin degradation. Generally, inhibition of Aβ activity can simply be detected by a decrease in cell death or an increase in cell survival after treatment of cells with an agent, as measured by one or more assays provided herein.

In some embodiments, inhibition of an Aβ activity can be measured, for example, by the difference in the activity before and after exposure of Aβ-treated neuronal cells to a suitable agent. The agent can be chosen from an antibody, a non-antibody polypeptide, a nucleic acid molecule, a carbohydrate, and a small molecule. Examples of antibodies include, but are not limited to, an antibody to FISH and/or a FISH interacting protein such as ADAM12. Examples of non-antibody polypeptides include, for example, deletion or substitution mutants of FISH and/or FISH interacting proteins, including dominant negative mutants of FISH and/or FISH interacting proteins. Examples of nucleic acid molecules include, for example, polynucleotides encoding deletion or substitution mutants of FISH and/or FISH interacting proteins, including dominant negative mutants of FISH and/or FISH interacting proteins. Additionally, antisense molecules and/or iRNA can be used as agents, where such antisense molecules hybridize to mRNA encoding FISH and/or a FISH interacting protein, thereby blocking the Aβ induced cell death pathway involving FISH and/or a FISH interacting protein.

The term "treating" or "treatment" refers to both therapeutic treatment and prophylactic or preventative measures. Those in need of treatment can include individuals already having a particular medical disorder, as well as those who may ultimately acquire the disorder (i.e., those needing preventative measures). Treatment can regulate Aβ activity or the level of Aβ to prevent or ameliorate clinical symptoms of at least one disease. The inhibitors and/or antibodies can function by, for example, preventing the phosphorylation of FISH, by blocking the interaction of FISH and its interacting proteins, such as ADAM12, and/or by reducing or blocking cleavage of ADAM12.

The term "patient" includes human and other mammalian subjects that receive either prophylactic or therapeutic treatment.

In the experiments leading to the present invention, a human homolog of the mouse FISH adapter protein (FISH) was isolated from cultured human cortical cells (HCC), which serve as an in vitro model for AD. Additionally, proteins that interact with FISH to mediate Aβ-induced cell death were also identified. An anti-phosphoTyrosine845 Epidermal Growth Factor Receptor (EGFR) antibody detected a phosphorylated form of FISH on western blots that was specific to cells treated with Aβ, thereby suggesting that phosphorylation of FISH can be induced by Aβ.

A similar approach can be used to identify other proteins, whose phosphorylation is induced by Aβ.

The invention further provides assays for identifying agents that modulate Aβ-induced cell death using an in vitro model for AD. Of particular interest are those agents that reduce or prevent Aβ-induced cell death. For example, in one embodiment, human cortical cultures (HCC) can be treated with Aβ, followed by treatment of cells with various agents to monitor their effect on the survival rate of such cells. Agents include, but are not limited to, antibodies that bind FISH and antibodies that bind ADAM12.

The present methods are useful for the prophylactic or therapeutic treatment of several diseases and conditions that are characterized by the presence of Aβ peptide. Such diseases include, for example, AD, Down's syndrome and cognitive impairment, type II diabetes, Parkinson's disease, amyloidoses such as hereditary or systemic amyloidoses, and diseases caused all or in part by prion infection.

Patients amenable to treatment include individuals at risk of disease but not showing symptoms, as well as individuals presently showing symptoms. In the case of AD, virtually anyone is at risk of suffering from AD if he or she lives long enough. The present methods are useful for individuals who have a known genetic risk of AD. Such individuals include those having relatives who have experienced this disease, and those whose risk is determined by analysis of genetic or biochemical markers. Genetic markers of risk toward AD include mutations in the APP gene, for example mutations at position 717 and positions 670 and 671 referred to as the Hardy and Swedish mutations, respectively (see Hardy, TINS, supra). Other markers of risk are mutations in-the presenilin genes, PS1 and PS2, and the gene for ApoE4, family history of AD, hypercholesterolemia, or arteriosclerosis. Individuals presently suffering from AD can be recognized from characteristic dementia, as well as the presence of the risk factors described above. In addition, a number of diagnostic tests are available for identifying individuals who have AD. These include measurement of cerebrospinal fluid (CSF) tau and Aβ42 levels. Elevated tau and decreased Aβ42 levels signify the presence of AD. Individuals suffering from AD can also be diagnosed by ADRDA criteria. In asymptomatic patients, treatment can begin at any age (e.g., about 10, about 20, about 30). Usually, however, it is not necessary to begin treatment until a patient reaches about 40, about 50, about 60, about 70, about 80 or about 90. Treatment typically entails multiple dosages over a period of time. In the case of Down's syndrome patients, treatment can begin prenatally by administering therapeutic agents to the mother; or treatment may begin shortly after birth.

In prophylactic applications, pharmaceutical compositions or medicaments can be administered to a patient susceptible to, or otherwise at risk of developing AD, in an amount sufficient to eliminate or reduce the risk, lessen the severity, or delay the onset of the disease, including biochemical, histological and/or behavioral symptoms of the disease, its complications and intermediate pathological phenotypes presenting during development of the disease.

In therapeutic applications, compositions or medicaments can be administered to a patient suspected of, or already suffering from a disease in an amount sufficient to cure, or at least partially arrest, the symptoms or progression of the disease (biochemical, histological, and/or behavioral), including its complications and intermediate pathological symptoms. An amount adequate to accomplish therapeutic or prophylactic treatment is defined as a therapeutically- or prophylactically-effective dose. In therapeutic regimes, the agent can be administered at intervals until symptoms of the disease disappear or significantly decrease. Optionally, administration can be continued to prevent recurrence. In prophylactic regimes, agents can also be administered at intervals, in some instances for the rest of a patient's life. Treatment can be monitored by assaying levels of administered agent, or by monitoring the response of the patient. The response can be monitored by ADRDA criteria and imaging of plaques in the brain of the patient (see WO 00/14810).

Effective doses of the compositions of the present invention, for the treatment of the above-described conditions vary depending upon many different factors, including means of administration, target site, physiological state of the patient, whether the patient is human or an animal, other medications administered, and whether treatment is prophylactic or therapeutic. Usually, the patient is a human; nonhuman mammals, including transgenic mammals, can also be treated. Treatment dosages can typically be titrated to optimize safety and efficacy.

Dosages of antibodies, nonantibody peptides and polypeptides, lipids, carbohydrates, and small molecules can range from about 0.0001 to about 100 mg/kg, and more usually about 0.01 to about 20 mg/kg, of the host body weight. For example, dosages can be about 1 mg/kg body weight or about 20 mg/kg body weight or within the range of about 1 to about 10 mg/kg. An exemplary treatment regime entails administration once per every two weeks or once a month or once every 3 to 6 months. In some methods, two, three, four or more monoclonal antibodies with different binding specificities can be administered simultaneously, in which case the dosage of each antibody administered falls within the ranges indicated. An antibody can usually be administered on multiple occasions. Intervals between single dosages can be weekly, monthly or yearly. In some methods, dosage of antibody can be adjusted to achieve a plasma antibody concentration of about 1 to about 1000 µg/ml, and in some methods about 25 to about 300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage can be administered at relatively infrequent intervals over a long period of time. Some patients continue to receive treatment for the rest of their lives. In therapeutic applications, a relatively high dosage at relatively short intervals can sometimes be required until the progression of the disease is reduced or terminated, and preferably until the patient shows partial or complete amelioration of the symptoms of the disease. Thereafter, the patient can be administered a prophylactic regime.

Doses for nucleic acid agents can range from about 10 ng to 1 g, about 100 ng to about 100 mg, about 1 µg to about 10 mg, or about 30 to about 300 µg DNA per patient. Nucleic acids encoding mutant forms of FISH and/or FISH interacting proteins, such as ADAM12, can be linked to regulatory elements, such as promoters and enhancers, that allow expression of the mutant forms in a cell and/or a patient. In some embodiments, promoters/enhancers that specifically cause expression in the brain are used. Promoters such as platelet-derived growth factor (PDGF), prion, or the neural enolase promoter are examples.

The linked regulatory elements and coding sequences can be cloned into a suitable vector. A number of viral vector systems are available including retroviral systems (see, e.g., Lawrie and Tumin, *Curr. Opin. Genet. Develop.*, 2:102-109 (1993)); adenoviral vectors (see, e.g., Bett et al., *J. Virol.*, 67:5911 (1993)); adeno-associated virus vectors (see, e.g., Zhou et al., *J. Exp. Med.*, 179:1867-75 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.*, 70:508-19 (1996)), Venezuelan equine encephalitis virus (see U.S. Pat. No. 5,643,576), rhabdoviruses, such as vesicular stomatitis virus (see WO 96/34625), herpes simplex virus, and papillomaviruses (Ohe et al., *Human Gene Therapy*, 6:325-33 (1995); Woo et al., WO 94/12629; and Xiao & Brandsma, *Nucleic Acids. Res.*, 24:2630-22 (1996)).

DNA can be packaged into liposomes. Suitable lipids and related analogs are described by U.S. Pat. Nos. 5,208,036, 5,264,618, 5,279,833, and 5,283,185.

Gene therapy vectors or naked DNA can be delivered in vivo by administration to an individual patient, typically by systemic administration (e.g., intravenous, intraperitoneal, nasal, gastric, intradermal, intramuscular, intrathecal, subdermal, or intracranial infusion) or topical application (see, e.g., U.S. Pat. No. 5,399,346). Vectors can include facilitating agents such as bupivacine (U.S. Pat. No. 5,593,970). DNA can also be administered using a gene gun. See Xiao & Brandsma, supra. The DNA is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc., Middleton, Wis. is suitable. Alternatively, naked DNA can pass through skin into the blood stream simply by spotting the DNA onto skin with chemical or mechanical irritation (see WO 95/05853).

In a further variation, nucleic acids can be delivered to cells ex vivo, such as cells explanted from an individual patient, followed by reimplantation of the cells into a patient, usually after selection for cells that have incorporated the vector.

The effect of antisense agents can be evaluated on the expression of the target nucleic acid (e.g., FISH and/or a FISH interacting protein) in a cell expressing the target nucleic acid at measurable levels. This can be routinely determined using, for example, PCR or Northern blot analysis.

Agents of the invention can be administered by parenteral, topical, intravenous, oral, subcutaneous, intrathecal, intraarterial, intracranial, intraperitoneal, intranasal, or intramuscular means for prophylactic and/or therapeutic treatment. In some methods, agents can be injected directly into a particular tissue where Aβ deposits have accumulated, for example, by intracranial injection. In some methods, intramuscular. injection or intravenous infusion can be employed for the administration of antibody. In some methods, particular therapeutic antibodies can be injected directly into the cranium. In some methods, antibodies can be administered as a sustained release composition or device, such as a Medipad™ device.

Agents of the invention can optionally be administered in combination with other agents. In the case of AD and Down's syndrome, in which amyloid deposits occur in the brain, agents of the invention can also be administered in conjunction with other agents that increase passage of the agents of the invention across the blood-brain barrier.

Agents of the invention can be administered as compositions comprising an active therapeutic agent and a variety of other pharmaceutically acceptable components. See Remington's Pharmaceutical Science (15th ed., Mack Publishing Company, Easton, Pa., 1980). The particular formulation employed depends on the intended mode of administration and the therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent can be selected so as not to negatively impact the biological activity of the combination. Examples of such diluents include, but are not limited to, distilled water, physiological phosphate-buffered saline, Ringer's solution, dextrose solution, and Hank's solution. In addition, the pharmaceutical composition or formulation can also include other carriers, adjuvants, or nontoxic, nontherapeutic, nonimmunogenic stabilizers, and the like.

Pharmaceutical compositions can also include large, slowly metabolized macromolecules such as proteins, polysaccharides such as chitosan, polylactic acids, polyglycolic acids, copolymers (such as latex functionalized Sepharose™ beads, agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically-acceptable diluent with a pharmaceutical carrier that can be a sterile liquid such as water, oils, saline, glycerol, or ethanol. Parenteral compositions for human administration can be sterile, substantially isotonic, and made under GMP conditions. Additionally, auxiliary substances, such as wetting or emulsifying agents, surfactants, pH buffering substances, and the like, can be present in compositions. Other components of pharmaceutical compositions can be those of petroleum, animal, vegetable, or synthetic origin, for example, peanut oil, soybean oil, and mineral oil. Glycols, such as propylene glycol or polyethylene glycol, can be liquid carriers, for example, for injectable solutions. Antibodies can be administered in the form of a depot injection or implant preparation that can be formulated in such a manner as to permit a sustained release of the active ingredient. An exemplary composition comprises monoclonal antibody at 5 mg/mL, formulated in aqueous buffer containing 50 mM L-histidine (optional), 150 mM NaCl, adjusted to a suitable pH with HCl.

Compositions can be prepared as injectables, either as liquid solutions or suspensions; solid forms suitable for solution in, or suspension in, liquid-vehicles prior to injection can also be prepared. The preparation also can be emulsified or encapsulated in liposomes or microparticles such as polylactide, polyglycolide, or copolymer for enhanced adjuvant effect, as discussed above (see Langer, Science, 249:1527-33 (1990) and Hanes et al., Advanced Drug Delivery Reviews, 28:97-119 (1997). The agents of this invention can be administered in the form of a depot injection or, implant preparation that can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of about 0.5% to about 10%, or about 1% to about 2%. Oral formulations include, but are not limited to, excipients such as pharmaceutical grades of mannitol, lactose, starch, magnesium stearate, sodium saccharine, cellulose, and magnesium carbonate. These compositions can take the form of solutions, suspensions, tablets, pills, capsules, sustained release formulations or powders and contain about 10% to about 95% of active ingredient, or about 25% to about 70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature, 391:851 (1998)). Coadministration can be achieved by using the components as a mixture or as linked molecules obtained by chemical crosslinking or expression as a fusion protein. Alternatively, transdermal delivery can be achieved using a skin patch or using transferosomes (Paul et al., Eur. J. Immunol., 25:3521-24 (1995); Cevc et al., Biochem. Biophys. Acta, 1368:201-15 (1998)).

The following examples provide various embodiments of the invention. One of ordinary skill in the art will recognize the numerous modifications and variations that can be performed without altering the spirit or scope of the present invention. Such modifications and variations are believed to be encompassed within the scope of the invention. The examples do not in any way limit the invention. It is understood that all of the numbers in the specification and claims are modified by the term about, as small changes in dosages, for example, would be considered to be within the scope of the invention.

EXAMPLES

The following materials and methods are for Examples 1-8, which follow.

Tissue culture

Tissue culture plates were coated with polyethyleneimine (PEI) in 150 mM sodium borate, pH 8.5, and incubated overnight at room temperature. Prior to adding cells, the wells were washed with phosphate-buffered salene (PBS) and Minimal Essential Media (MEM with 10% fetal bovine serum (FBS)) was added until cells were ready for plating. Human fetal cerebral cortex (E13-E16) was rinsed with Hank's Balanced Salt Solution (HBSS). Tissue was triturated in 1 mg of DNAse in HBSS. This suspension was filtered through a 100 micron nylon cell strainer and centrifuged at 250×g for 5 minutes. The cells were resuspended in trypsin and incubated at 37° C. for 20 minutes. Modified Minimal Essential Media (MMEM with 10% FBS and 1 mg of DNase) was added and the cells were resuspended; then collected again by centrifugation. Cells were resuspended in MMEM containing B27, and plated in washed PEI-coated plates at 125,000 cells/well in 96 well plates or at 2.5 million cells/well in 6 well plates. The human cortical cultures (HCC) were incubated for 3 weeks with biweekly medium exchanges prior to treatment.

Aβ Generation

Aβ was generated by adding double distilled water (ddH$_2$O) to Aβ to make up a 1 mM stock. This was aged for 3 days at 37° C., aliquoted, and stored frozen at −20° C. Soluble Aβ was made by adding DMSO to Aβ to make a 7.5 mM stock, sonicating for 30 minutes, aliquoting, and freezing at −20° C. Neurotoxic Aβ was generated by adding ddH$_2$O to Aβ, aliquoting, and freezing at −20° C.

FISH Immunoprecipitations from HCC Lysates

Cells were washed, lysed with 25 mM Hepes, pH 7.5, 1% Triton X-100, 0.1% SDS, 150 mM NaCl, 0.5 mM EDTA, 0.5 mM EGTA, and passed through a 26 gauge needle three times. Insoluble material was removed by centrifugation at 15,000 rpm for 15 minutes at 4° C. Lysates were pre-cleared on rabbit anti-mouse (RAM) antibody coupled to protein A beads and immunoprecipitated with FISH-specific antibodies or with antipY845EGFR antibodies. In certain experiments, HCC in 6 well plates were labeled with 100 µCi/ml $^{35}$S-methionine in methionine-free medium overnight prior to lysis. In some experiments, FISH protein was phosphorylated with $^{32}$P.

Aβ Immunofluorescence

HCC treated with Aβ for 72 hours were fixed with 4% paraformaldehyde, stained with 5 μg/ml anti-Aβ-3D6-biotin, and visualized with 10 μg/ml streptavidin-FITC (Jackson).

Aβ Neurotoxicity in Human Cortical Neurons

HCC were pretreated with antibodies or ligands for 30 minutes in neuronal medium (MEM) supplemented with glutamine and penicillin/streptomycin (basal media). One micromolar Aβ in basal medium was added for 1 hour. The medium was removed and the HCC were treated with antibodies or ligands and 20 μM soluble Aβ in basal medium for 3 days. At three days, the toxicity was determined by incubating in 10% alamar blue in basal medium for two hours. Fluorescence levels were measured relative to control and Aβ treated wells in triplicate.

Aβ Induction of FISH Phosphorylation

Neurotoxic Aβ was added to HCC in 6-well plates in basal media supplemented with N-2 for 0 minutes to 24 hours. HCC was placed on wet-ice, washed with PBS, lysed with 25 mM Hepes, pH 7.5, 1% Triton X-100, 0.1% SDS, 150 mM NaCl, 0.5 mM EDTA, and 0.5 mM EGTA, and passed through a 26 gauge needle 3 times. Insoluble material was removed by centrifugation at 15,000 rpm for 15 minutes at 4° C. Lysates were precleared on protein A beads and FISH was immunoprecipitated using anti-FISH or an anti-pY845EGFR antibody and protein A beads. Immunoprecipitates were washed 3 times with 1 ml of 25 mM Hepes, pH 7.5, 1% Triton X-100 150 mM NaCl, 0.5 mM EDTA, and 0.5 mM EGTA. Immunoprecipitated samples were separated on 8% tris-glycine gels (Novex) and Western blotted with anti-phosphotyrosine 845 EGFR.

The present examples use an in vitro tissue culture model of Aβ plaques that form on hippocampal and cortical neurons in Alzheimer's disease (AD) and exhibit the associated neurotoxicity. The model uses primary human cortical neuronal cultures to represent the neurons effected in AD as closely as possible. Addition of Aβ to these cultures results in a reproducible Aβ meshwork that forms over 1-3 days on the neurons and subsequently causes toxicity in the neurons. Aβ incubated on plates without HCC also stained as a meshwork but consistently showed a more uniform pattern with extensions that were shorter, thinner, and more linear than those seen on HCC.

Example 1

Identification and Purification of a Human Homolog of the Mouse FISH Adapter Protein HCC cells were treated with Aβ, as discussed above, and the whole cell lysates were treated with an anti-phosphotyrosine845 EGFR antibody to detect proteins that may be phosphorylated on tyrosine residues upon treatment of cells with Aβ. A western blot of the cell lysates revealed a phosphoprotein (p165) that appeared in HCC cells only upon treatment with Aβ, suggesting that phosphorylation of this protein was induced by Aβ. FIG. 1 shows a representative western blot of one such experiment which demonstrates cross-reactivity of the p165 protein with an anti-pY845EGFR antibody in presence of Aβ (lane 3). Immunoprecipitation of EGFR revealed that this protein was not phosphorylated EGFR but a yet unknown protein (data not shown). Treatment of cell lysates with a phosphotyrosine-specific phosphatase (LAR) resulted in a disappearance of the band corresponding to the p165 protein (lane 1)

Figure 2A:
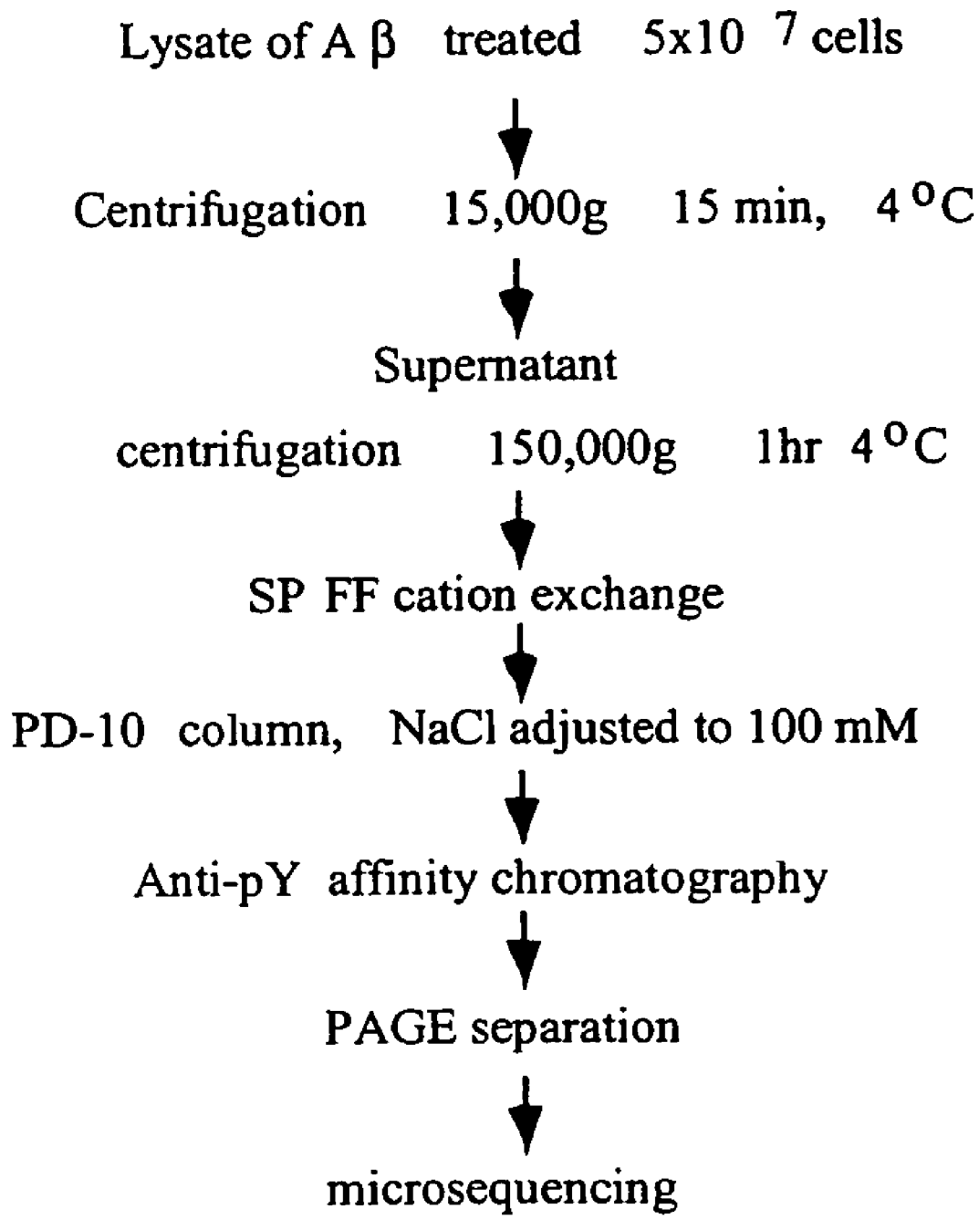
FIG. 2A is a flow-chart depicting the various steps involved in the purification of the p165 protein.
Figure 2B:
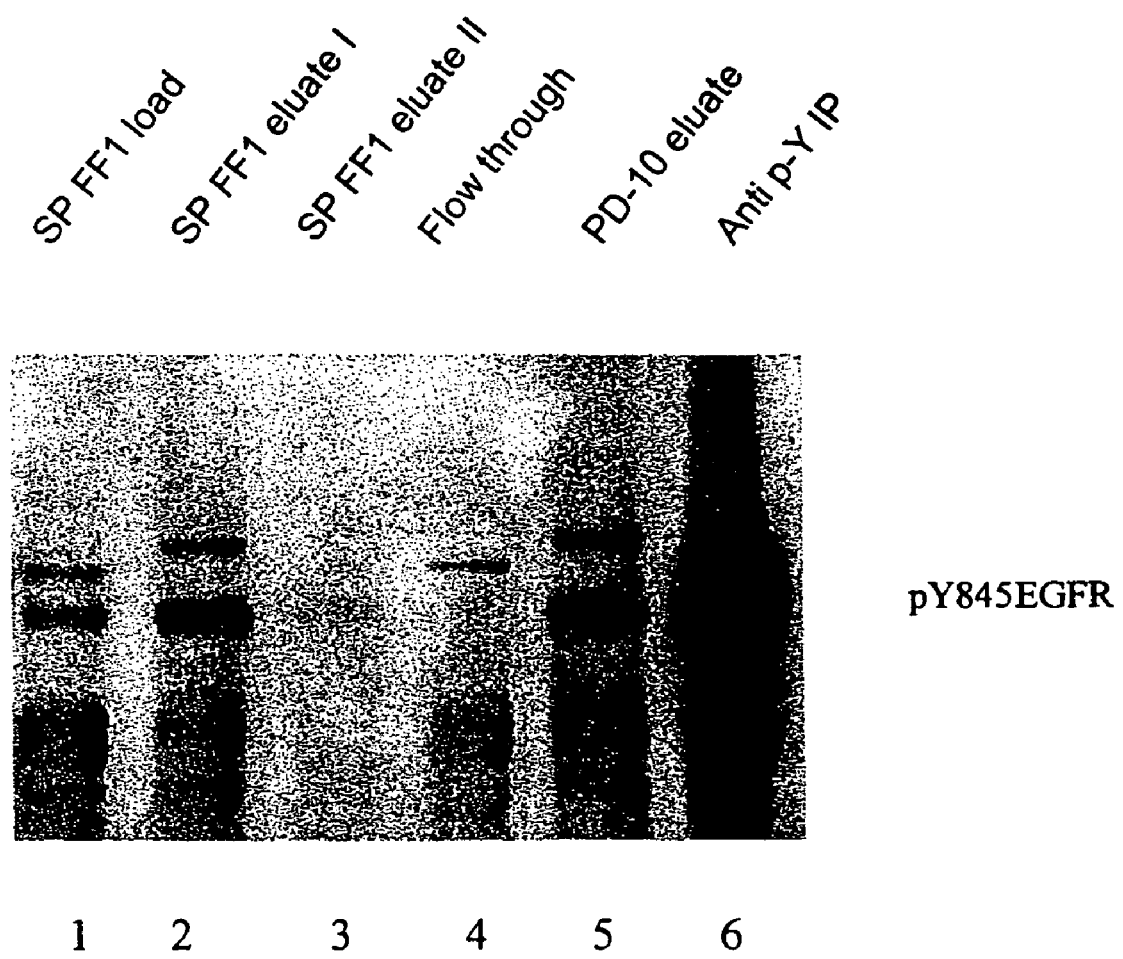
FIG. 2B (lanes 1-6) shows a western blot with eluates from various steps of a protein purification protocol to purify p165 from whole cell lysates of cultured human cortical cells treated with Aβ. The western blot depicts enrichment of the eluates for the p165 protein, detected with an anti-pY845EGFR antibody.

An empirically defined protocol was used for the purification of p165 from whole cell lysates of HCC cells treated with Aβ. FIG. 2A shows a flow chart with the various steps used in the purification process and FIG. 2B shows a western blot that depicts enrichment of p165 in eluates obtained from various steps in the purification process.

Figure 3:
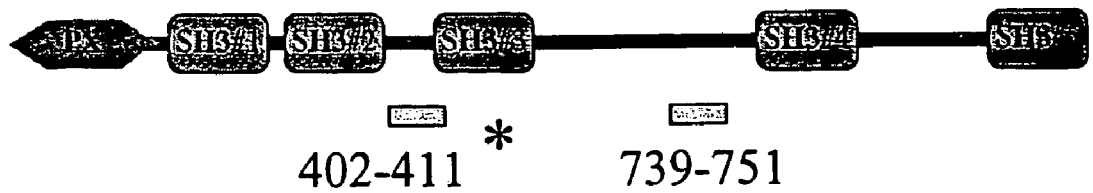
FIG. 3 is a schematic representation of the p165 protein, identified as a human homolog of the mouse FISH adapter protein, which includes a Phox homology (PX) domain and five Src homology 3 (SH3) domains. Two peptides corresponding to amino acid residues 402-411 and 739-751 were sequenced.

The p165 protein was microsequenced and the deduced amino acid sequence was used to search known databases. The p165 protein was subsequently identified as a human homolog of a murine protein called FISH adapter protein. (Lock et al., The EMBO J., 17: 4346-4357 (1998)). A schematic representation of p165 is shown in FIG. 3. Based on the deduced amino acid sequence of the p165 protein, the protein is predicted to have an N-terminal Phox-homology (PX) domain and five Src homology 3 (SH3) domains. The fifth Src homology domain of the mouse FISH (SH3 domain #5) has been previously reported to interact with members of the ADAM family of proteins, including ADAM12, ADAM15, and ADAM 19. (Abram et al., J. Biol. Chem., 278:16844-16851 (2003)).

Example 2

FISH is Phosphorylated in HCC Cells in Response to AD Treatment

Figure 4A:
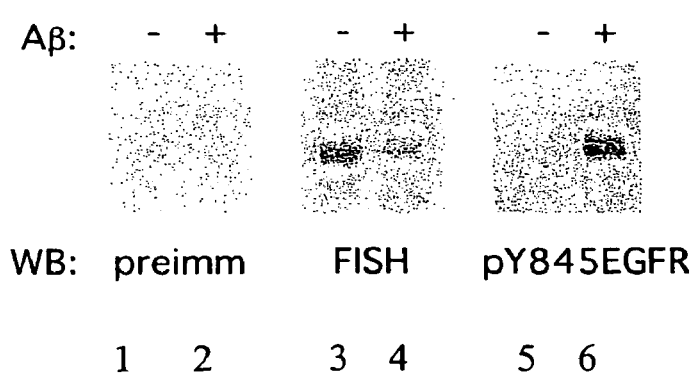
FIG. 4A shows a western blot depicting the immunoprecipitation of endogenous FISH from cultured human cortical cells and the phosphorylation of FISH in the presence of Aβ, as detected with an anti-pY845EGFR antibody.

HCC cells were treated with Aβ, as discussed above, and endogenous FISH was immunoprecipitated, also as discussed above. Results of one such representative experiment are shown in FIGS. 4.

Immunoprecipitations and subsequent detection by western blotting were performed both in absence and presence of Aβ. FIG. 4 (lanes 1 and 2) depict a negative control where no FISH is detected, as expected. Lanes 3 and 4 show the presence of endogenous FISH both in Aβ treated and untreated HCC cells, as detected using an anti-FISH antibody. Lanes 5 and 6 show that FISH is phosphorylated on one or more tyrosine residues only upon treatment with Aβ. Accordingly, this experiment suggests that phosphorylation of endogenous FISH is induced by Aβ.

Figure 4B:
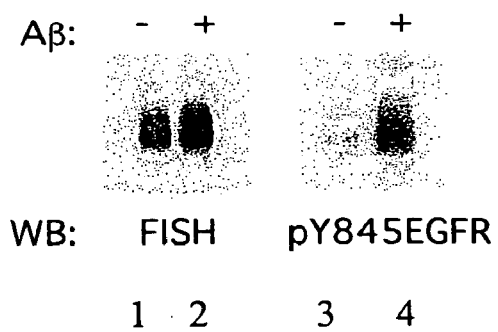
FIG. 4B shows a western blot depicting the phosphorylation of FISH protein expressed from an adenovirus construct in cultured human cortical cells upon treatment with Aβ, as detected with an anti-pY845EGFR antibody.

The results of this experiment were further substantiated by investigating the phosphorylation of exogenous FISH expressed in HCC from an adenovirus construct. As shown in FIG. 4B, Aβ treatment led to robust phosphorylation of adenovirally expressed FISH (lane 4).

Example 3

PX Deletion Mutants of FISH are Phosphorylated in an Aβ Independent Manner

In order to determine which domain(s) of FISH were involved in Aβ-induced phosphorylation of FISH, various mutant forms of FISH were generated. Two mutant forms carried deletions of the N-terminal PX domain. These were designated 14FL, which was missing the first 166 amino acids of FISH, and 615, which was missing the first 347 amino acids of FISH. These mutant forms were expressed in HCC cells either treated with Aβ or left untreated and subsequently immunoprecipitated FISH protein was subsequently detected by western blotting using the anti-phosphotyrosine845

Figure 5:
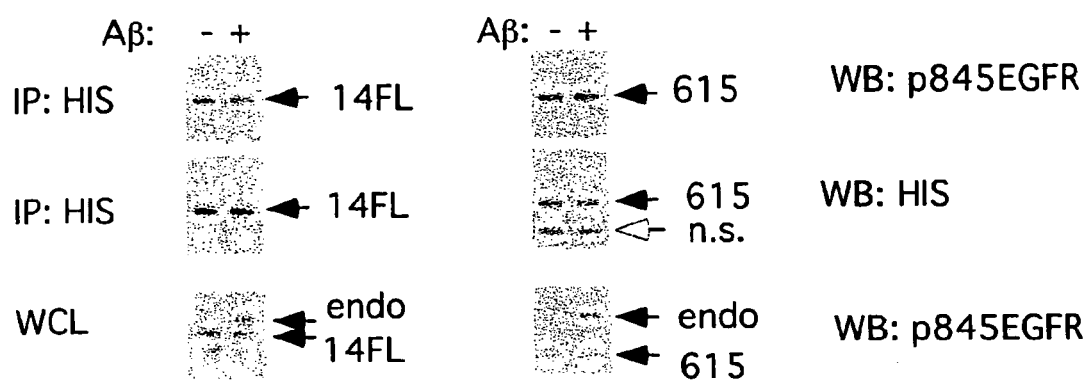
FIG. 5 shows western blots depicting the phosphorylation of Phox homology deletion mutants of FISH (14FL-includes a deletion of 166 amino acids from the N-terminus of FISH; 615-includes a deletion 347 amino acids from the N-terminus of FISH) in an Aβ-independent manner.

EGFR. As shown in FIG. 5, both of the PX deletion mutants (14FL and 615) were phosphorylated independent of treatment with Aβ.

Example 4

The Presence of the Fifth SH3 Domain in FISH is Necessary but Not Essential for Neurotoxicity and PX has a Protective Effect on the Neurons Various N and C terminal mutant forms of FISH were generated and tested for their toxic effect on neurons. Initially, three mutant forms were tested. The FISH 981-1105 mutant form was missing the PX as well as the first four SH3 domains but contained the fifth SH3 domain, which has previously been reported to interact with members of the ADAM family of proteins. The FISH 348-1105 mutant form was missing the PX domain, but included the third, forth, and fifth SH3 domains. The FISH 348-911 mutant form was missing the PX as well as the fifth SH3 domain.

Figure 6:
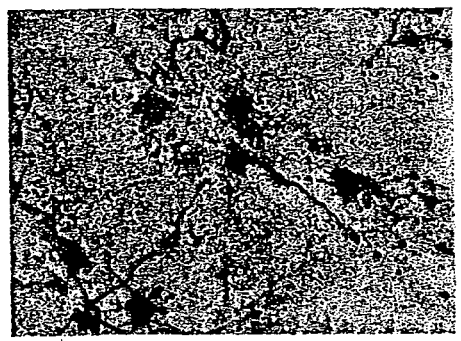
FIGS. 6A-6C are micrographs depicting inverted images of Enhanced Green Fluorescent Protein (EGFP) positive neurons expressing deletion mutants of FISH.
Figure 6:
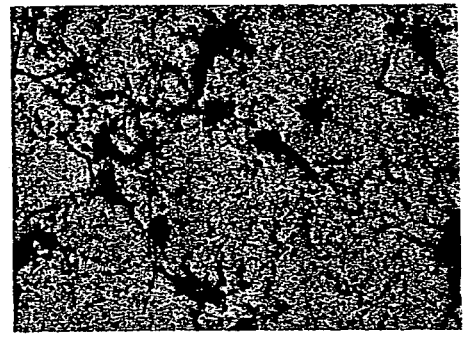
Figure 6:
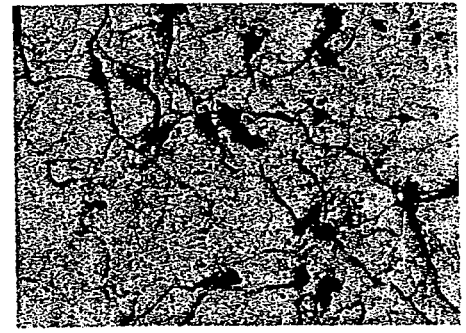

FIG. 6 shows micrographs of inverted images of neurons that were infected with adenoviruses encoding the above-described FISH mutant forms. In all instances, the neurons were positive for EGFP, which was used as a marker for the infected cells. As shown in FIG. 6, the neurons that were infected with the mutant forms that contained the fifth SH3 domain (FISH 981-1105 and FISH 348-1105) showed more cell death relative to the neurons that were infected with mutant forms that were missing the SH3 domain (FISH 348-911).

To further delineate the importance of the various domains on the effect of FISH on neurotoxicity, additional deletion mutants of FISH were generated. All the mutant forms are summarized below in Table 1 along with the degree of neurotoxicity after neurons were infected with adenovirues encoding the various mutant forms.

TABLE 1

| FISH protein (amino acids) | Toxicity |
|---|---|
| FLPX (1-1105) | − |
| 14FL (167-1105) | ++ |
| 615 (348-1105) | ++++ |
| Hinc (348-911) | + |
| 232 (981-1105) | +/− |
| 14PCR (167-431) | − |
| 14Sma (167-721) | +/− |

Figure 7:
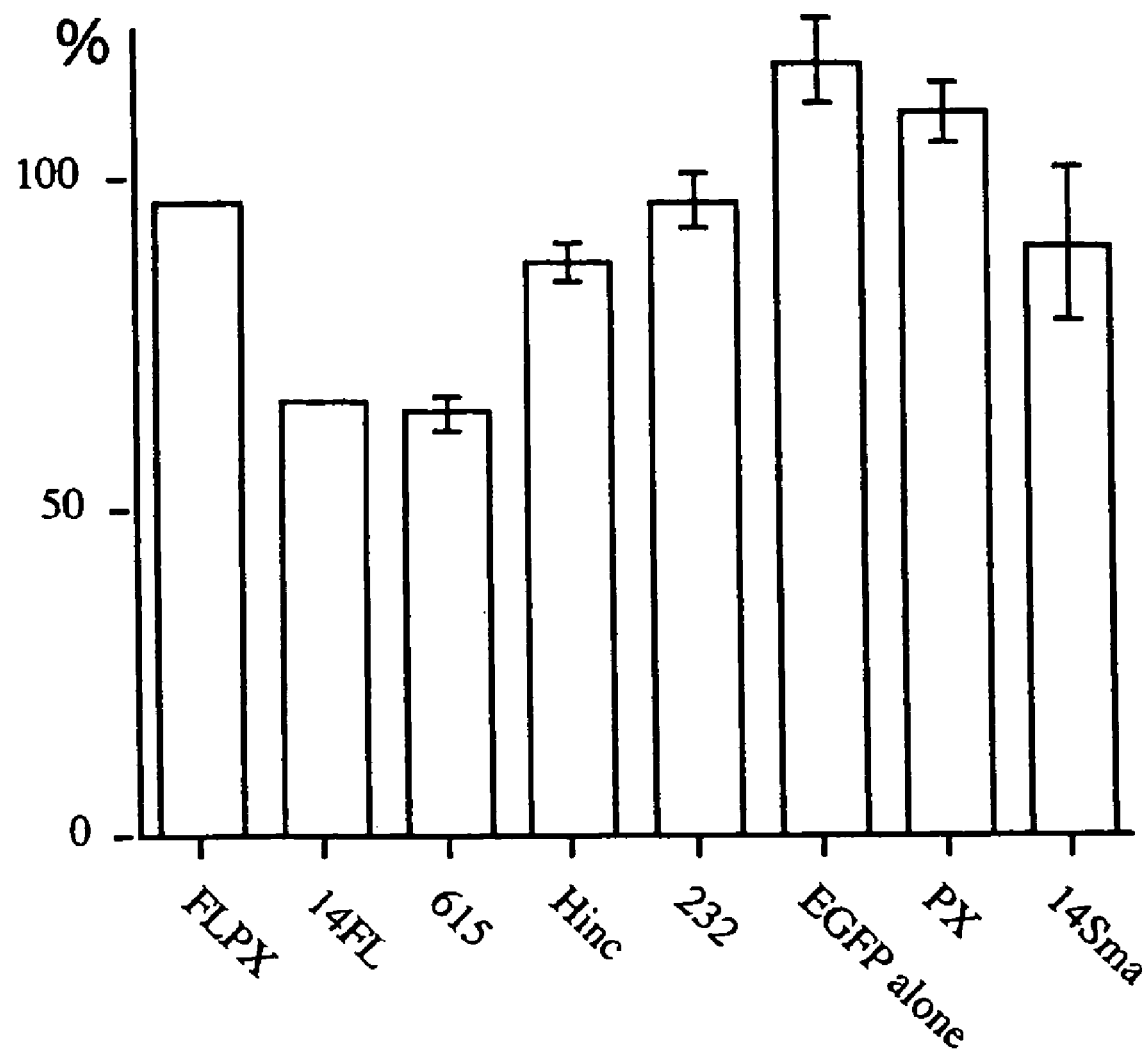
FIG. 7 is a bar graph showing the survival rate of neuronal cells infected with mutant forms of FISH expressed by adenovirus constructs.

As summarized in Table 1, the full-length FISH protein (FLPX) appeared to have little or no toxic effect on HCC, whereas the mutant forms that included the fifth SH3 domain were the most neurotoxic, in particular, 14FL and 651. Also, the 14PCR mutant form, which included the PX domain but was missing the fifth SH3 domain, also produced little or no toxicity. The results of one such experiment are also graphically depicted in FIG. 7, which shows the percentage of cells that survived after being infected with adenoviruses encoding the various forms of FISH, relative to non-infected cells. The percentage survival of these cells was determined as described above in Materials and Methods.

Example 5

FISH Adapter Protein Re-Localizes in Cells Upon Treatment with Aβ

Figure 8:
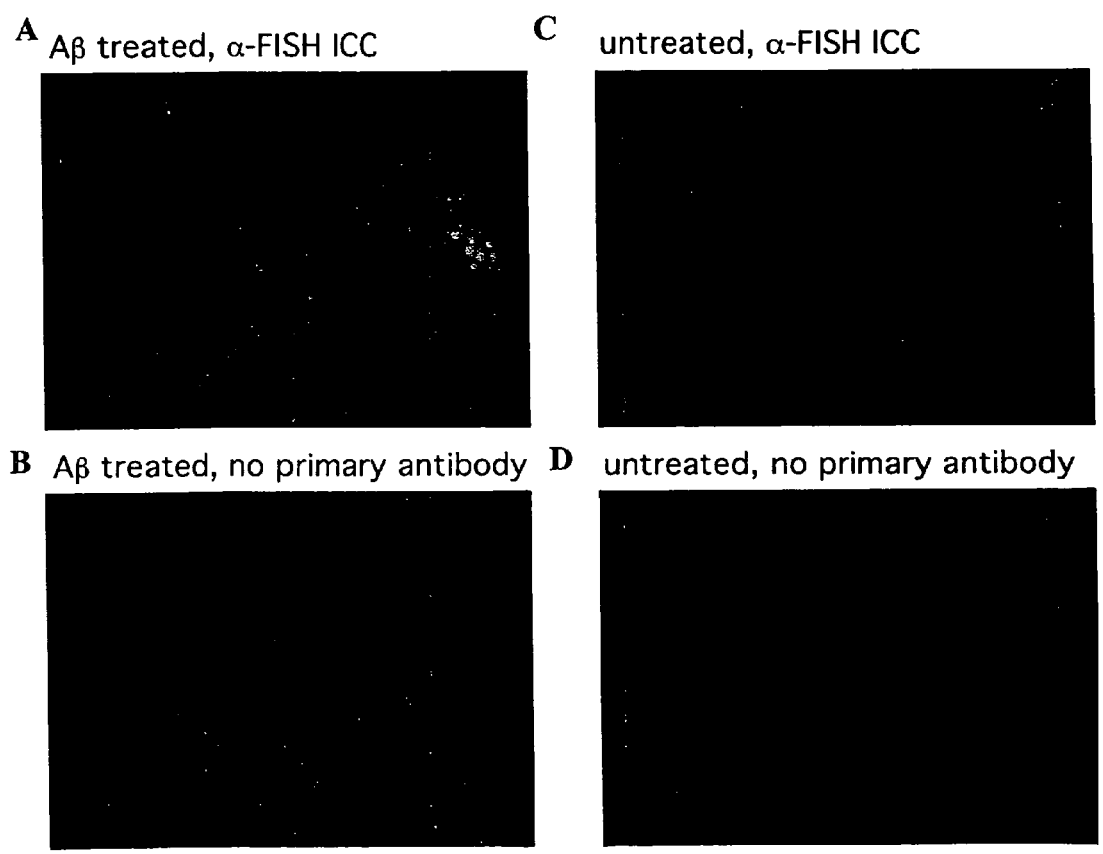
FIGS. 8A-8D are immunofluorescence images of HCC cells showing the localization of FISH in the presence and absence of Aβ, as detected using an antibody to FISH.

Tyrosine phosphorylation of FISH upon treatment with Aβ suggests that the Aβ neurotoxic signal may be mediated through FISH tyrosine phosphorylation. In order to further investigate the role of FISH in Aβ-induced cell death, HCC cells were examined for the subcellular localization of FISH in untreated cells as well as in cells that were treated for 6 hours with Aβ. Endogenous FISH was detected by immunofluorescence using a primary anti-FISH antibody followed by a Red Cy3 labeled anti-rabbit antibody. A blue DAPI stain was used to detect nuclei. The FISH adapter protein was re-localized in Aβ treated cells, as shown in FIG. 8A, compared to the localization in untreated cells, as shown in FIG. 8C.

Example 6

ADAM12 is Cleaved During Aβ-Induced Toxicity

Previously, it was reported that FISH, especially the fifth SH3 domain of FISH, interacts with members of the ADAM family of proteins, including ADAM12, 15, and 19. However, the significance, if any, of these interactions in Aβ-induced toxicity is unknown. Because the fifth SH3 domain of FISH appears to be important in Aβ-induced toxicity, as discussed above, the interaction of FISH with members of the ADAM family of proteins was investigated.

Figures 9A, 9B:
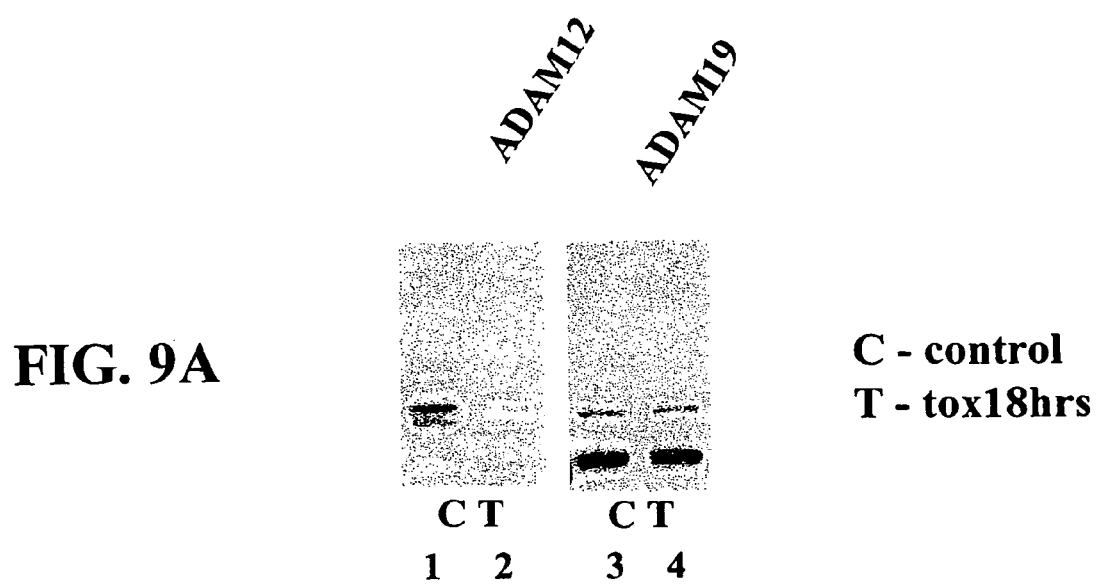
FIG. 9A shows a western blot depicting the expression of ADAM12 and ADAM19 in lysates of cultured human cortical cells either left untreated (C) or in cells treated for about 18 hours with Aβ (T).
FIG. 9B shows a western blot depicting the degradation of heregulin (HRG) in lysates of cultured human cortical cells either left untreated (C) or in cells treated for about 18 hours with Aβ (T).

Self-cleavage of ADAMs accompanies activation of their protease activity. Western blotting for ADAM12 and 19 in whole cell lysates of HCC cells either left untreated or treated for 18 hours with Aβ, revealed that ADAM12 is in fact cleaved in cells treated with Aβ, suggesting that cleavage of ADAM12 and subsequent activation may play a role in Aβ-induced toxicity. The results of one such representative experiment are shown in FIG. 9A, which is a western blot depicting ADAM12 cleavage during Aβ-induced toxicity in HCC cells, as indicated by lower levels of ADAM12 in Aβ treated cells (lane 2), whereas levels of ADAM19 do not change in the presence or absence of Aβ (lanes 3 and 4).

That Aβ-induced toxicity is accompanied by cleavage and subsequent activation of ADAM12 was confirmed by investigating the degradation of heregulin (HRG), which is a transmembrane precursor protein known to be cleaved by metalloproteases of the ADAM family. Degradation of pro-HRG was investigated in HCC cells either left untreated or treated with Aβ. As shown in FIG. 9B, Aβ treatment induced degradation of pro-HRG relative to cells that were left untreated.

Example 7

ADAM12 Deletion Mutants Block FISH Induced Toxicity

As discussed above, the PX domain of FISH has a protective effect on neurons. However, FISH mutants containing the fifth SH3 domain are the most toxic. Since, the fifth SH3 domain has been shown to interact with members of the ADAM family and ADAM12 appears to be activated by, the effect of ADAM12 deletion mutants that are missing the metalloprotease domain (ADAM12D198-415 and ADAM12D198-501) was investigated on the toxic effect of a FISH deletion mutant, which was missing the PX domain but contained the fifth SH3 domain.

Figure 10:
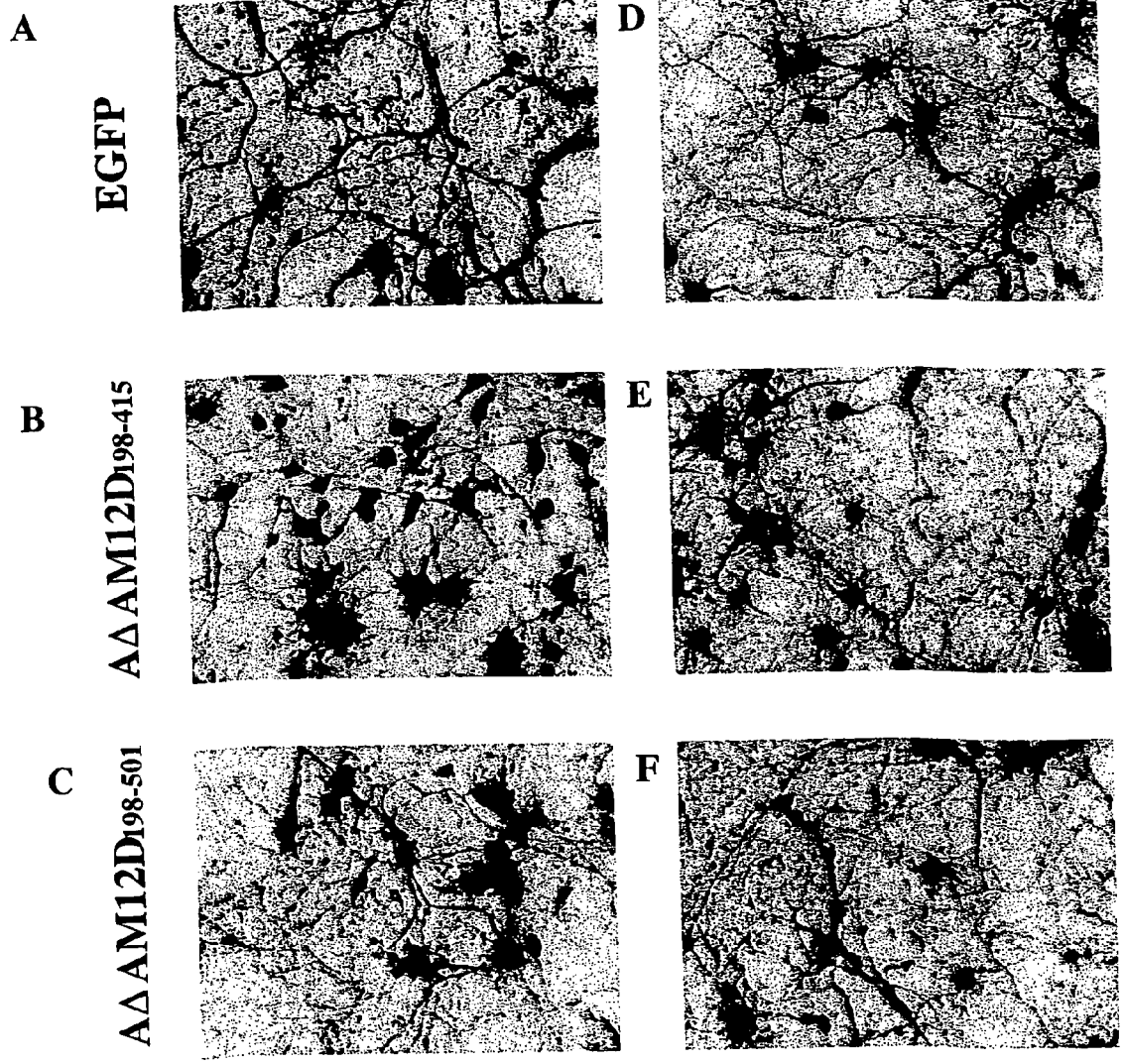
FIGS. 10A-10F are micrographs of inverted images of EGFP-positive neurons (10D) and EGFP-positive neurons expressing a deletion mutant of FISH (FISH 348-1105) (10A), which further express ADAM12 deletion mutants: ADAM12del 198-415 in 10B and 10E and ADAM12del 198-501 in 10C and 10F.

HCC cells were either infected with an adenovirus encoding the FISH Mutant (FISH 348-1105) or encoding EGFP, and subsequently infected with an adenovirus encoding either EGFP, ADAM12D198-415, or ADAM12D198-501. The effect on neuronal toxicity was examined. As shown in micrographs of the cells in FIG. 10, the FISH mutant induced toxicity in the presence of Aβ, (10D) compared with the cells expressing the ADAM12 deletion mutants(10B and 10C), thereby suggesting that these mutants block the toxic effect of the FISH deletion mutant.

Example 8

ADAM12 Deletion Mutants Block Aβ Induced Toxicity

Figure 11:
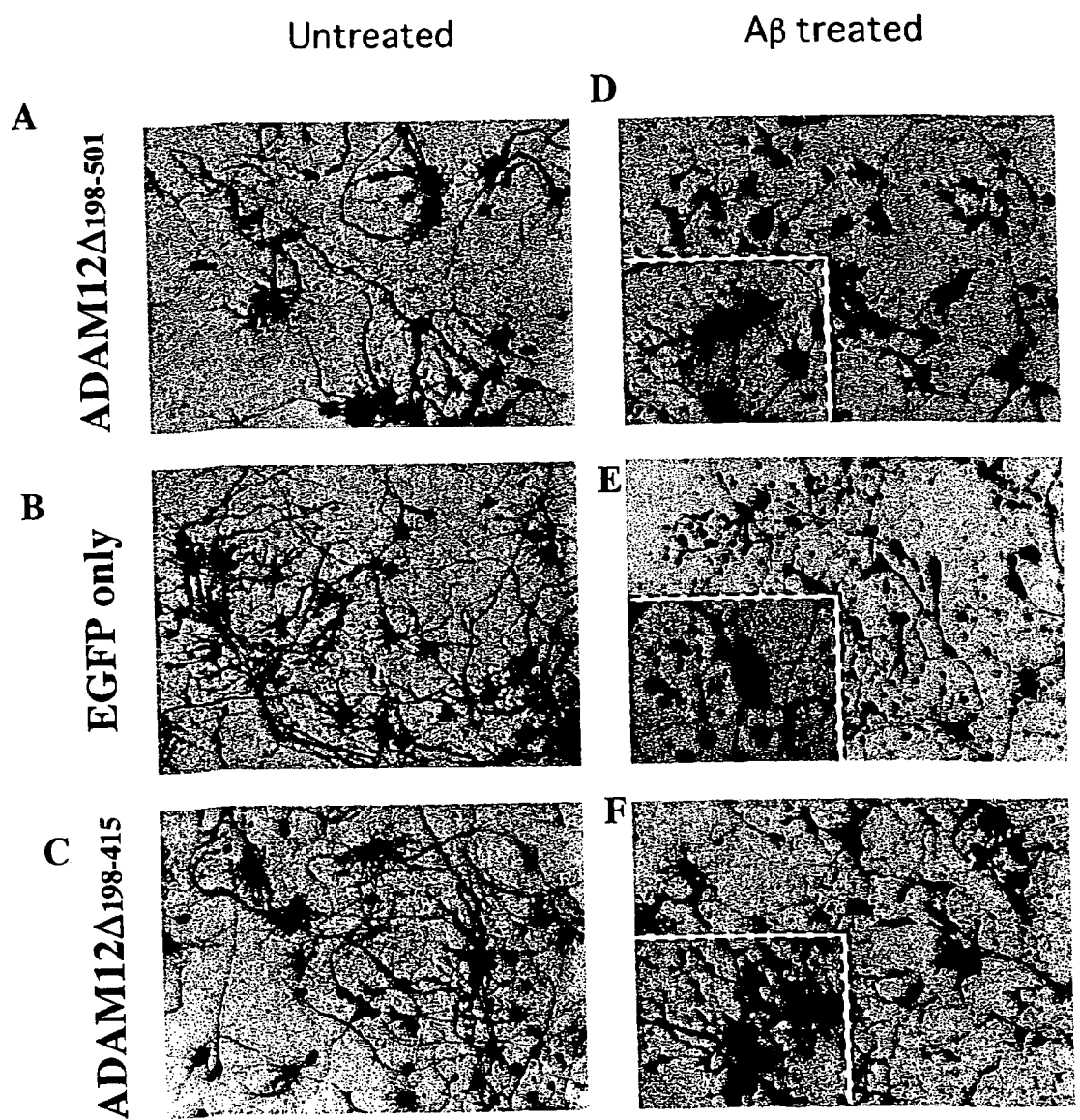
FIGS. 11A-11F are micrographs of inverted images of neurons, either left untreated (11A, B, and C) or treated with Aβ (11D, E, and F), and further expressing either ADAM12del 198-501 in 11A and D, EGFP in 10B and E, or ADAMdel 198-415 in 11C and F.

In addition to examining the effect of the ADAM12 deletion mutants on FISH induced toxicity, their effect on Aβ-induced neuronal toxicity was also examined. The results of a representative experiment are shown in FIG. 11, which shows micrographs of HCC cells transfected with adenoviruses encoding various ADAM12 deletion mutants in both untreated cells and cells that had been treated with Aβ. As shown in FIG. 11, the ADAM12 deletion mutants (ADAM12del 198-501 in 11A and ADAM12del 198-415 in 11F) blocked the toxic effect of Aβ.

All publications and patent applications cited above are incorporated by reference in their entirety for all purposes to the same extent as if each individual publication or patent application were specifically and individually indicated to be so incorporated by reference. If the disclosure of any of the publications and patent applications incorporated by reference conflicts with the disclosure of the instant application, the instant application controls. Although the present invention has been described in some detail by way of illustration and example for purposes of clarity and understanding, it will be apparent that certain changes and modifications can be practiced within the scope of the appended claims.

Many modifications and variations of this invention can be made without departing from its spirit and scope, as will be apparent to those skilled in the art. The specific embodiments described herein are offered by way of example only and are not meant to be limiting in any way. Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying an agent that inhibits Aβ-induced neuronal cell death, comprising:

contacting neuronal cells with a candidate agent and Aβ; and measuring a decrease in phosphorylation of a scaffolding protein that contains five SH3 domains (FISH adapter protein), a decrease in ADAM12 (SEQ ID NO:4) cleavage, or a decrease in heregulin degradation in the neuronal cells relative to control cells contacted with Aβ without the candidate agent, wherein the decrease indicates the candidate agent inhibits Aβ-induced neuronal cell death.

* * * * *

```
SEQUENCE LISTING

<160> NUMBER OF SEQ ID NOS: 4

<210> SEQ ID NO 1
<211> LENGTH: 3728
<212> TYPE: DNA
<213> ORGANISM: mus musculus

<400> SEQUENCE: 1
cgggcgggca ggctagcgga gccggcggcg cgcgagggaa ggggcgcccc ccaggcccac      60
gggagcagcc tgggacgcac ggagccctcg tgccctccgg gacagtcgcc tgccccggag     120
cctcagctgt aggcgcccgg agcctcggcg gcgagtagcg cgtgggacag gggtggcgtg     180
taactgcagg aaccggggca accggagaag gagccggaac ccggccggga tgagaaggtg     240
acgccgccgg ggggcgccac tcgctttgtg gggacgatgc tcgcctactg cgtgcaagat     300
gccaccgtgg tggacgtgga gaagcggagg agcccctcta aacactatgt atacattatc     360
aacgtgacct ggtctgactc cacctcccag actatctacc ggaggtacag caagttcttc     420
gacctgcaga tgcagcttct ggataagttt cctattgaag gtggccagaa ggatccgaag     480
caaaggatta ttccctttct tccaggcaag atcctcttcc ggagaagcca catccgcgac     540
gtggctgtga agagactaaa gcccatcgat gaatactgca gggcgcttgt ccggctgccg     600
ccccacattt cacagtgtga cgaagtcttc cggttctttg aggcacggcc tgaggatgtc     660
aaccctccaa aagaagacta tggcagttcc aagaggaaat cagtgtggtt gtccagctgg     720
gctgagtctc ccaagaagga cgtgacaggt gccgacacca acgccgagcc catgatcctg     780
gaacagtacg tggtggtgtc caactataag aaacaagaga actcggagct gagcctccag     840
gccggggagg tggtagatgt catcgagaag aacgaaagcg gctggtggtt tgtgagcaca     900
tctgaagagc aaggtttgggt ccccgccacc tacttggagg cccagaatgg cacacgagac     960
gactcggaca tcaacacctc caagactggg gaagtgtcca agagacgcaa ggcacacctg    1020
cggcgcctgg atcgccggtg gaccctgggc gggatggtca acaggcagca cagccgagaa    1080
```

```
gagaagtatg tcactgtgca gccctacacc agccagagca aagacgagat cggcttcgag    1140
aagggtgtca ccgtggaggt gattcgaaag aacctggaag gctggtggta catcaggtac    1200
ctcggcaaag agggttgggc accagcgtcc tacctgaaga aggccaagga tgacctgccg    1260
acccggaaga agaacctggc gggtccggtg agatcatag gaacattat ggagatcagc      1320 aaccttctca caagaaggc atctggggat aaggaggctc cggctgaagg cgagggatcc     1380
gaggccccca tcaccaagaa agagatcagc ttaccgatcc tctgcaacgc ctccaatggc    1440
agcgccttgg ccattcccga gaggaccaca tccaagctag cccagggctc cccagctgtg    1500
gccaggatcg cccctcagag ggcccagatc agctccccaa atctgaggac aagacctccc    1560
ccgcgcagag aatccagcct ggggttccag ctgccaaagc cgccagagcc cccttctgtt    1620
gaggtagaat actacaccat tgctgaattc cagtcctgca tttctgacgg gatcagcttt    1680
cgaggcggac agaaggcaga ggtcatcgac aagaactcgg gtggttggtg gtacgtgcag    1740
atcggggaga aggagggctg gccccagcc tcatacattg acaagcgcaa gaaacccaac     1800
ctcagccgcc gaaccagcac tctgacgcgg cccaaggtgc cgccgcctgc gcccccagc    1860 aagcctaagg aggctgagga gaatcctgtg ggtgcctgtg agagccaggg ctccccactg    1920
aaggttaaat acgaggaacc cgagtatgac gtccctgcct ttggctttga ctcagagccc    1980
gagatgaatg aagagccttc aggggacaga ggttcaggtg acaagcatcc cgcccagccc    2040
cgaaggatct cgcctgcctc ttccctgcaa cgggcccatt tcaaggtggg tgagtcttct    2100
gaggacgtgg ccctggaaga ggagaccatc tatgagaatg agggcttcag gccatacaca    2160
gaagacaccc tgtctgccag aggctcctct ggggacagtg actcccctgg gagctcctct    2220 ttgtccctttg ccgtgaaaaa ctcccctaaa tcagattccc ccaaatcctc atcactccta    2280
aagctcaaag cagagaagaa tgcccaggca gaactgggga aaaaccagtc caacatctcc    2340
ttctcctcct ctgtcaccat cagcaccacc tgttcttcct cctcctcgtc gtcctccttg    2400
tccaagaaca atggtgacct gaaaccacgt tctgcctcag atgcaggtat ccgtgacacc    2460
cctaaggttg ggaccaagaa agatcctgat gtgaaggccg ggctggcctc ctgcgcccga    2520
gccaagccat ccgtgagacc aaagccagtc ctgaaccgag cggagtctca aagccaggag    2580
aagatggata ttagttcctt acggcgccag ctgaggccca caggccagct ccgggggggc    2640
ctcaagggct ctaggagtga ggactcagag ctgcctccac agatggcttc tgagggatcc    2700
aggcgaggtt ctgcggacat catccctctc acggccacca ctcccccgtg tgtccccaaa    2760
aaggaatggg aagggcaagg cgccacctac gtgacgtgca gcgcctatca gaaggtccag    2820
gactcggaga tcagcttccc cgaaggcgcc gaggtgcacg tgctggagaa ggcggtaagt    2880
gggtggtggt acgtgaggtt tggggagctg gagggctggg ctccttccca ctacttggtg    2940
gccgaggaga accagcaacc tgacacagct agcaaagagg gagacacagg aaagagctcg    3000
cagaacgagg gcaagtcaga cagcctggaa aagattgaga agcgtgtgca ggcgctcaac    3060
actgtgaacc agagcaagag ggccacccca cccatcccct cgaagcctcc cggggggcttc    3120 ggcaagacct cgggcaccgt agcggtgaag atgaggaacg ggtccggca agtggccgtc    3180 aggcccccaat ctgtgtttgt gtctccgcca cccaaggaca caacctgtc ctgtgcccttt    3240 cggaggaacg agtcgctaac ggccaccgac agcctcagag gtgtccgcag gaactcctcc    3300
tttagcaccg cacggtcagc agccgctgag gccaagggcc gctggccga gcgggctgcc    3360 agccagggct cagaatcgcc cctgctgcct acccagcgca aaggcatccc tgtctccccc    3420
```

-continued

```
gtgcgtccca agcccataga gaagtcccag tttatccaca acaacctcaa ggatgtgtac    3480
atctcgattg cagactatga gggggacgaa gagacggctg gcttccagga gggggtgtcc    3540
atggaggtgc tggagaagaa ccccaatggc tggtggtact gccagatcct ggatgaggtg    3600
aagcccttca agggctgggt accctccaac taccttgaga agaagaacta atagcacagg    3660
gtccttccag actcaacgtg ctgccttggc tgccactgga tgagctgcgg cacgccagac    3720
acgggccg                                                              3728
```

<210> SEQ ID NO 2
<211> LENGTH: 1124
<212> TYPE: PRT
<213> ORGANISM: mus musculus

<400> SEQUENCE: 2

```
Met Leu Ala Tyr Cys Val Gln Asp Ala Thr Val Val Asp Val Glu Lys
1               5                   10                  15

Arg Arg Ser Pro Ser Lys His Tyr Val Tyr Ile Ile Asn Val Thr Trp
            20                  25                  30

Ser Asp Ser Thr Ser Gln Thr Ile Tyr Arg Arg Tyr Ser Lys Phe Phe
        35                  40                  45

Asp Leu Gln Met Gln Leu Leu Asp Lys Phe Pro Ile Glu Gly Gly Gln
    50                  55                  60

Lys Asp Pro Lys Gln Arg Ile Ile Pro Phe Leu Pro Gly Lys Ile Leu
65                  70                  75                  80

Phe Arg Arg Ser His Ile Arg Asp Val Ala Val Lys Arg Leu Lys Pro
                85                  90                  95

Ile Asp Glu Tyr Cys Arg Ala Leu Val Arg Leu Pro Pro His Ile Ser
            100                 105                 110

Gln Cys Asp Glu Val Phe Arg Phe Phe Glu Ala Arg Pro Glu Asp Val
        115                 120                 125

Asn Pro Pro Lys Glu Asp Tyr Gly Ser Ser Lys Arg Lys Ser Val Trp
    130                 135                 140

Leu Ser Ser Trp Ala Glu Ser Pro Lys Lys Asp Val Thr Gly Ala Asp
145                 150                 155                 160

Thr Asn Ala Glu Pro Met Ile Leu Glu Gln Tyr Val Val Ser Asn
                165                 170                 175

Tyr Lys Lys Gln Glu Asn Ser Glu Leu Ser Leu Gln Ala Gly Glu Val
            180                 185                 190

Val Asp Val Ile Glu Lys Asn Glu Ser Gly Trp Trp Phe Val Ser Thr
        195                 200                 205

Ser Glu Glu Gln Gly Trp Val Pro Ala Thr Tyr Leu Glu Ala Gln Asn
    210                 215                 220

Gly Thr Arg Asp Asp Ser Asp Ile Asn Thr Ser Lys Thr Gly Glu Val
225                 230                 235                 240

Ser Lys Arg Arg Lys Ala His Leu Arg Leu Asp Arg Trp Thr
                245                 250                 255

Leu Gly Gly Met Val Asn Arg Gln His Ser Arg Glu Glu Lys Tyr Val
            260                 265                 270

Thr Val Gln Pro Tyr Thr Ser Gln Ser Lys Asp Glu Ile Gly Phe Glu
        275                 280                 285

Lys Gly Val Thr Val Glu Val Ile Arg Lys Asn Leu Glu Gly Trp Trp
    290                 295                 300

Tyr Ile Arg Tyr Leu Gly Lys Glu Gly Trp Ala Pro Ala Ser Tyr Leu
305                 310                 315                 320
```

-continued

Lys Lys Ala Lys Asp Asp Leu Pro Thr Arg Lys Lys Asn Leu Ala Gly
            325                 330                 335

Pro Val Glu Ile Ile Gly Asn Ile Met Glu Ile Ser Asn Leu Leu Asn
            340                 345                 350

Lys Lys Ala Ser Gly Asp Lys Glu Ala Pro Ala Glu Gly Glu Gly Ser
            355                 360                 365

Glu Ala Pro Ile Thr Lys Lys Glu Ile Ser Leu Pro Ile Leu Cys Asn
            370                 375             380

Ala Ser Asn Gly Ser Ala Leu Ala Ile Pro Glu Arg Thr Thr Ser Lys
385                 390                 395                 400

Leu Ala Gln Gly Ser Pro Ala Val Ala Arg Ile Ala Pro Gln Arg Ala
            405                 410                 415

Gln Ile Ser Ser Pro Asn Leu Arg Thr Arg Pro Pro Arg Arg Glu
            420                 425                 430

Ser Ser Leu Gly Phe Gln Leu Pro Lys Pro Pro Glu Pro Ser Val
            435                 440                 445

Glu Val Glu Tyr Tyr Thr Ile Ala Glu Phe Gln Ser Cys Ile Ser Asp
            450                 455                 460

Gly Ile Ser Phe Arg Gly Gly Gln Lys Ala Glu Val Ile Asp Lys Asn
465                 470                 475                 480

Ser Gly Gly Trp Trp Tyr Val Gln Ile Gly Glu Lys Glu Gly Trp Ala
            485                 490                 495

Pro Ala Ser Tyr Ile Asp Lys Arg Lys Lys Pro Asn Leu Ser Arg Arg
            500                 505             510

Thr Ser Thr Leu Thr Arg Pro Lys Val Pro Pro Ala Pro Pro Ser
            515                 520             525

Lys Pro Lys Glu Ala Glu Asn Pro Val Gly Ala Cys Glu Ser Gln
            530                 535             540

Gly Ser Pro Leu Lys Val Lys Tyr Glu Glu Pro Glu Tyr Asp Val Pro
545                 550                 555                 560

Ala Phe Gly Phe Asp Ser Glu Pro Glu Met Asn Glu Glu Pro Ser Gly
            565                 570                 575

Asp Arg Gly Ser Gly Asp Lys His Pro Ala Gln Pro Arg Arg Ile Ser
            580                 585                 590

Pro Ala Ser Ser Leu Gln Arg Ala His Phe Lys Val Gly Glu Ser Ser
            595                 600                 605

Glu Asp Val Ala Leu Glu Glu Glu Thr Ile Tyr Glu Asn Glu Gly Phe
            610                 615                 620

Arg Pro Tyr Thr Glu Asp Thr Leu Ser Ala Arg Gly Ser Ser Gly Asp
625                 630                 635                 640

Ser Asp Ser Pro Gly Ser Ser Leu Ser Leu Ala Val Lys Asn Ser
            645                 650                 655

Pro Lys Ser Asp Ser Pro Lys Ser Ser Leu Leu Lys Leu Lys Ala
            660                 665                 670

Glu Lys Asn Ala Gln Ala Glu Leu Gly Lys Asn Gln Ser Asn Ile Ser
            675                 680                 685

Phe Ser Ser Ser Val Thr Ile Ser Thr Thr Cys Ser Ser Ser Ser Ser
            690                 695             700

Ser Ser Ser Leu Ser Lys Asn Asn Gly Asp Leu Lys Pro Arg Ser Ala
705                 710                 715                 720

Ser Asp Ala Gly Ile Arg Asp Thr Pro Lys Val Gly Thr Lys Lys Asp
            725                 730                 735

-continued

Pro Asp Val Lys Ala Gly Leu Ala Ser Cys Ala Arg Ala Lys Pro Ser
            740                 745                 750

Val Arg Pro Lys Pro Val Leu Asn Arg Ala Glu Ser Gln Ser Gln Glu
        755                 760                 765

Lys Met Asp Ile Ser Ser Leu Arg Arg Gln Leu Arg Pro Thr Gly Gln
    770                 775                 780

Leu Arg Gly Gly Leu Lys Gly Ser Arg Ser Glu Asp Ser Glu Leu Pro
785                 790                 795                 800

Pro Gln Met Ala Ser Glu Gly Ser Arg Arg Gly Ser Ala Asp Ile Ile
            805                 810                 815

Pro Leu Thr Ala Thr Thr Pro Pro Cys Val Pro Lys Lys Glu Trp Glu
        820                 825                 830

Gly Gln Gly Ala Thr Tyr Val Thr Cys Ser Ala Tyr Gln Lys Val Gln
    835                 840                 845

Asp Ser Glu Ile Ser Phe Pro Glu Gly Ala Glu Val His Val Leu Glu
850                 855                 860

Lys Ala Val Ser Gly Trp Trp Tyr Val Arg Phe Gly Glu Leu Glu Gly
865                 870                 875                 880

Trp Ala Pro Ser His Tyr Leu Val Ala Glu Glu Asn Gln Gln Pro Asp
            885                 890                 895

Thr Ala Ser Lys Glu Gly Asp Thr Gly Lys Ser Ser Gln Asn Glu Gly
        900                 905                 910

Lys Ser Asp Ser Leu Glu Lys Ile Glu Lys Arg Val Gln Ala Leu Asn
    915                 920                 925

Thr Val Asn Gln Ser Lys Arg Ala Thr Pro Ile Pro Ser Lys Pro
    930                 935                 940

Pro Gly Gly Phe Gly Lys Thr Ser Gly Thr Val Ala Val Lys Met Arg
945                 950                 955                 960

Asn Gly Val Arg Gln Val Ala Val Arg Pro Gln Ser Val Phe Val Ser
            965                 970                 975

Pro Pro Pro Lys Asp Asn Asn Leu Ser Cys Ala Leu Arg Arg Asn Glu
        980                 985                 990

Ser Leu Thr Ala Thr Asp Ser Leu Arg Gly Val Arg Arg Asn Ser Ser
    995                 1000                1005

Phe Ser Thr Ala Arg Ser Ala Ala Ala Glu Ala Lys Gly Arg Leu
    1010                1015                1020

Ala Glu Arg Ala Ala Ser Gln Gly Ser Glu Ser Pro Leu Leu Pro
    1025                1030                1035

Thr Gln Arg Lys Gly Ile Pro Val Ser Pro Val Arg Pro Lys Pro
    1040                1045                1050

Ile Glu Lys Ser Gln Phe Ile His Asn Asn Leu Lys Asp Val Tyr
    1055                1060                1065

Ile Ser Ile Ala Asp Tyr Glu Gly Asp Glu Glu Thr Ala Gly Phe
    1070                1075                1080

Gln Glu Gly Val Ser Met Glu Val Leu Glu Lys Asn Pro Asn Gly
    1085                1090                1095

Trp Trp Tyr Cys Gln Ile Leu Asp Glu Val Lys Pro Phe Lys Gly
    1100                1105                1110

Trp Val Pro Ser Asn Tyr Leu Glu Lys Lys Asn
    1115                1120

<210> SEQ ID NO 3
<211> LENGTH: 3369
<212> TYPE: DNA

<213> ORGANISM: Homo sapiens

<400> SEQUENCE: 3

```
ggactgctgg ccgtggatcc atttcacagg cctgccttct ctcactaacg ctcttcctag      60
tccccgggcc aactcggaca gtttgctcat ttattgcaac ggtcaaggct ggcttgtgcc     120
agaacggcgc gcgcgcgcgc acgcacgcac acacacgggg ggaaacttttt ttaaaaatga    180
aaggctagaa gagctcagcg gcggcgcggg cgctgcgcga gggctccgga gctgactcgc     240
cgaggcagga aatccctccg gtcgcgacgc ccggccccgg ctcggcgccc gcgtgggatg     300
gtgcagcgct cgccgccggg cccgagagct gctgcactga aggccggcga cgatggcagc     360
gcgcccgctg cccgtgtccc ccgcccgcgc cctcctgctc gccctggccg gtgctctgct     420
cgcgccctgc gaggcccgag gggtgagctt atggaaccaa ggaagagctg atgaagttgt     480
cagtgcctct gttcggagtg gggacctctg gatcccagtg aagagcttcg actccaagaa     540
tcatccagaa gtgctgaata ttcgactaca acgggaaagc aaagaactga tcataaatct     600
ggaaagaaat gaaggtctca ttgccagcag tttcacggaa acccactatc tgcaagacgg     660
tactgatgtc tccctcgctc gaaattacac gggtcactgt tactaccatg acatgtacg     720
gggatattct gattcagcag tcagtctcag cacgtgttct ggtctcaggg gacttattgt     780
gtttgaaaat gaaagctatg tcttagaacc aatgaaaagt gcaaccaaca gatacaaact     840
cttcccagcg aagaagctga aaagcgtccg gggatcatgt ggatcacatc acaacacacc     900
aaacctcgct gcaaagaatg tgtttccacc accctctcag acatgggcaa gaaggcataa     960
aagagagacc ctcaaggcaa ctaagtatgt ggagctggtg atcgtggcag acaaccgaga    1020
gtttcagagg caaggaaaag atctggaaaa agttaagcag cgattaatag agattgctaa    1080
tcacgttgac aagttttaca gaccactgaa cattcggatc gtgttggtag cgtggaagt    1140
gtggaatgac atggacaaat gctctgtaag tcaggaccca ttcaccagcc tccatgaatt    1200
tctggactgg aggaagatga agcttctacc tcgcaaatcc catgacaatg cgcagcttgt    1260
cagtgggggtt tatttccaag ggaccaccat cggcatggcc ccaatcatga gcatgtgcac    1320
ggcagaccag tctgggggaa ttgtcatgga ccattcagac aatccccttg gtgcagccgt    1380
gaccctggca catgagctgg ccacaatttt cgggatgaat catgcacac tggacagggg    1440
ctgtagctgt caaatggcgg ttgagaaagg aggctgcatc atgaacgctt ccaccgggta    1500
cccatttccc atggtgttca gcagttgcag caggaaggac ttggagacca gcctggagaa    1560
aggaatgggg gtgtgcctgt ttaacctgcc ggaagtcagg gagtctttcg ggggccagaa    1620
gtgtgggaac agatttgtgg aagaaggaga ggagtgtgac tgtggggagc cagaggaatg    1680
tatgaatcgc tgctgcaatg ccaccacctg taccctgaag ccggacgctg tgtgcgcaca    1740
tgggctgtgc tgtgaagact gccagctgaa gcctgcagga acagcgtgca gggactccag    1800
caactcctgt gacctcccag agttctgcac aggggccagc cctcactgcc cagccaacgt    1860
gtacctgcac gatgggcact catgtcagga tgtggacggc tactgctaca atggcatctg    1920
ccagactcac gagcagcagt gtgtcacgct ctggggacca ggtgctaaac ctgcccctgg    1980
gatctgcttt gagagagtca attctgcagg tgatccttat ggcaactgtg gcaaagtctc    2040
gaagagttcc tttgccaaat gcgagatgag agatgctaaa tgtggaaaaa tccagtgtca    2100
aggaggtgcc agccggccag tcattggtac caatgccgtt tccatagaaa caaacatccc    2160
cctgcagcaa ggaggccgga ttctgtgccg ggggacccac gtgtacttgg gcgatgacat    2220
gccggaccca gggcttgtgc ttgcaggcac aaagtgtgca gatggaaaaa tctgcctgaa    2280
```

-continued

```
tcgtcaatgt caaaatatta gtgtctttgg ggttcacgag tgtgcaatgc agtgccacgg    2340 cagagggtg tgcaacaaca ggaagaactg ccactgcgag gcccactggg cacctcccct     2400
ctgtgacaag tttggctttg gaggaagcac agacagcggc cccatccggc aagcagggaa    2460
agaagcaagg caggaagctg cagagtccaa cagggagcgc ggccagggcc aggagcccgt    2520
gggatcgcag gagcatgcgt ctactgcctc actgacactc atctgagccc tcccatgaca    2580
tggagaccgt gaccagtgct gctgcagagg aggtcacgcg tccccaaggc ctcctgtgac    2640
tggcagcatt gactctgtgg ctttgccatc gtttccatga caacagacac aacacagttc    2700
tcggggctca ggaggggaag tctagcctac caggcacgtc tgcagaaaca gtgcaaggaa    2760
gggcagcgac ttcctggttg agcttctgct aaaacatgga catgcttcag tgctgctcct    2820
gagagagtag caggttacca ctctggcagg ccccagccct gcagcaagga ggaagaggac    2880
tcaaaagtct ggcctttcac tgagcctcca cagcagtggg ggagaagcaa gggttgggcc    2940
cagtgtcccc tttccccagt gacacctcag ccttggcagc cctgatgact ggtctctggc    3000
tgcaacttaa tgctctgata tggcttttag catttattat atgaaaatag cagggtttta    3060 gttttttaatt tatcagagac cctgccaccc attccatctc catccaagca aactgaatgg    3120
caatgaaaca aactggagaa gaaggtagga gaaagggcgg tgaactctgg ctctttgctg    3180
tggacatgcg tgaccagcag tactcaggtt tgagggtttg cagaaagcca gggaacccac    3240
agagtcacca acccttcatt taacaagtaa gaatgttaaa aagtgaaaac aatgtaagag    3300
cctaactcca tcccccgtgg ccattactgc ataaaataga gtgcatttga aataaaaaaa    3360
aaaaaaaaa                                                             3369
```

<210> SEQ ID NO 4
<211> LENGTH: 737
<212> TYPE: PRT
<213> ORGANISM: Homo sapiens

<400> SEQUENCE: 4

```
Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Gln Gly Arg Ala Asp Glu Val Val Ser Ala Ser Val Arg
        35                  40                  45

Ser Gly Asp Leu Trp Ile Pro Val Lys Ser Phe Asp Ser Lys Asn His
    50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Gly His Cys Tyr Tyr His Gly His Val Arg Gly Tyr Ser Asp Ser
        115                 120                 125

Ala Val Ser Leu Ser Thr Cys Ser Gly Leu Arg Gly Leu Ile Val Phe
    130                 135                 140

Glu Asn Glu Ser Tyr Val Leu Glu Pro Met Lys Ser Ala Thr Asn Arg
145                 150                 155                 160

Tyr Lys Leu Phe Pro Ala Lys Lys Leu Lys Ser Val Arg Gly Ser Cys
                165                 170                 175
```

```
Gly Ser His His Asn Thr Pro Asn Leu Ala Ala Lys Asn Val Phe Pro
            180                 185                 190

Pro Pro Ser Gln Thr Trp Ala Arg Arg His Lys Arg Glu Thr Leu Lys
            195                 200                 205

Ala Thr Lys Tyr Val Glu Leu Val Ile Val Ala Asp Asn Arg Glu Phe
210                 215                 220

Gln Arg Gln Gly Lys Asp Leu Glu Lys Val Lys Gln Arg Leu Ile Glu
225                 230                 235                 240

Ile Ala Asn His Val Asp Lys Phe Tyr Arg Pro Leu Asn Ile Arg Ile
                245                 250                 255

Val Leu Val Gly Val Glu Val Trp Asn Asp Met Asp Lys Cys Ser Val
            260                 265                 270

Ser Gln Asp Pro Phe Thr Ser Leu His Glu Phe Leu Asp Trp Arg Lys
            275                 280                 285

Met Lys Leu Leu Pro Arg Lys Ser His Asp Asn Ala Gln Leu Val Ser
            290                 295                 300

Gly Val Tyr Phe Gln Gly Thr Thr Ile Gly Met Ala Pro Ile Met Ser
305                 310                 315                 320

Met Cys Thr Ala Asp Gln Ser Gly Gly Ile Val Met Asp His Ser Asp
                325                 330                 335

Asn Pro Leu Gly Ala Ala Val Thr Leu Ala His Glu Leu Gly His Asn
            340                 345                 350

Phe Gly Met Asn His Asp Thr Leu Asp Arg Gly Cys Ser Cys Gln Met
            355                 360                 365

Ala Val Glu Lys Gly Gly Cys Ile Met Asn Ala Ser Thr Gly Tyr Pro
370                 375                 380

Phe Pro Met Val Phe Ser Ser Cys Ser Arg Lys Asp Leu Glu Thr Ser
385                 390                 395                 400

Leu Glu Lys Gly Met Gly Val Cys Leu Phe Asn Leu Pro Glu Val Arg
                405                 410                 415

Glu Ser Phe Gly Gly Gln Lys Cys Gly Asn Arg Phe Val Glu Glu Gly
            420                 425                 430

Glu Glu Cys Asp Cys Gly Glu Pro Glu Glu Cys Met Asn Arg Cys Cys
            435                 440                 445

Asn Ala Thr Thr Cys Thr Leu Lys Pro Asp Ala Val Cys Ala His Gly
            450                 455                 460

Leu Cys Cys Glu Asp Cys Gln Leu Lys Pro Ala Gly Thr Ala Cys Arg
465                 470                 475                 480

Asp Ser Ser Asn Ser Cys Asp Leu Pro Glu Phe Cys Thr Gly Ala Ser
                485                 490                 495

Pro His Cys Pro Ala Asn Val Tyr Leu His Asp Gly His Ser Cys Gln
            500                 505                 510

Asp Val Asp Gly Tyr Cys Tyr Asn Gly Ile Cys Gln Thr His Glu Gln
            515                 520                 525

Gln Cys Val Thr Leu Trp Gly Pro Gly Ala Lys Pro Ala Pro Gly Ile
530                 535                 540

Cys Phe Glu Arg Val Asn Ser Ala Gly Asp Pro Tyr Gly Asn Cys Gly
545                 550                 555                 560

Lys Val Ser Lys Ser Ser Phe Ala Lys Cys Glu Met Arg Asp Ala Lys
                565                 570                 575

Cys Gly Lys Ile Gln Cys Gln Gly Gly Ala Ser Arg Pro Val Ile Gly
            580                 585                 590
```

-continued

```
Thr Asn Ala Val Ser Ile Glu Thr Asn Ile Pro Leu Gln Gln Gly Gly
        595                 600                 605

Arg Ile Leu Cys Arg Gly Thr His Val Tyr Leu Gly Asp Asp Met Pro
        610                 615                 620

Asp Pro Gly Leu Val Leu Ala Gly Thr Lys Cys Ala Asp Gly Lys Ile
625                 630                 635                 640

Cys Leu Asn Arg Gln Cys Gln Asn Ile Ser Val Phe Gly Val His Glu
                645                 650                 655

Cys Ala Met Gln Cys His Gly Arg Gly Val Cys Asn Asn Arg Lys Asn
                660                 665                 670

Cys His Cys Glu Ala His Trp Ala Pro Pro Phe Cys Asp Lys Phe Gly
        675                 680                 685

Phe Gly Gly Ser Thr Asp Ser Gly Pro Ile Arg Gln Ala Gly Lys Glu
        690                 695                 700

Ala Arg Gln Glu Ala Ala Glu Ser Asn Arg Glu Arg Gly Gln Gly Gln
705                 710                 715                 720

Glu Pro Val Gly Ser Gln Glu His Ala Ser Thr Ala Ser Leu Thr Leu
                725                 730                 735

Ile
```